(12) United States Patent
Okawa et al.

(10) Patent No.: US 9,133,854 B2
(45) Date of Patent: Sep. 15, 2015

(54) CENTRIFUGAL BLOOD PUMP DEVICE

(75) Inventors: Atsushi Okawa, Higashkurume (JP); Takehisa Mori, Ashigarakami-gun (JP)

(73) Assignee: Thoratec Corporation, Pleasanton, CA (US)

( * ) Notice: Subject to any disclaimer, the term of this patent is extended or adjusted under 35 U.S.C. 154(b) by 0 days.

(21) Appl. No.: 13/617,381

(22) Filed: Sep. 14, 2012

(65) Prior Publication Data
US 2013/0243623 A1 Sep. 19, 2013

Related U.S. Application Data

(63) Continuation of application No. PCT/JP2011/054134, filed on Feb. 24, 2011.

(30) Foreign Application Priority Data

Mar. 26, 2010 (JP) .................................. 2010-071796

(51) Int. Cl.
*F04D 29/047* (2006.01)
*A61M 1/10* (2006.01)
(Continued)

(52) U.S. Cl.
CPC ........... *F04D 29/0473* (2013.01); *A61M 1/101* (2013.01); *A61M 1/1015* (2014.02);
(Continued)

(58) Field of Classification Search
CPC . F04D 29/047; F04D 29/0473; F04D 29/051; F04D 29/0513; F04D 13/06; F04D 13/0666; F04D 29/048; F04D 29/473; F16C 33/107; F16C 32/0692; A61M 1/101; A61M 1/1015; A61M 1/1017

USPC ......................... 417/423.12, 423.13; 384/112
See application file for complete search history.

(56) References Cited

U.S. PATENT DOCUMENTS

| 1,093,868 A | 4/1914 | Leighty |
|---|---|---|
| 2,684,035 A | 7/1954 | Kemp |

(Continued)

FOREIGN PATENT DOCUMENTS

| CN | 102239334 A | 11/2011 |
|---|---|---|
| CN | 102341600 A | 2/2012 |

(Continued)

OTHER PUBLICATIONS

International Search Report (PCT/ISA/210) issued on Apr. 12, 2011, by the Japanese Patent Office as the International Searching Authority for International Application No. PCT/JP2011/054134.

(Continued)

*Primary Examiner* — Peter J Bertheaud
*Assistant Examiner* — Dnyanesh Kasture
(74) *Attorney, Agent, or Firm* — Kilpatrick Townsend & Stockton LLP

(57) ABSTRACT

A centrifugal blood pump device includes a housing, a centrifugal pump section having an impeller which rotates in the housing to send blood by centrifugal force upon rotation, an impeller rotation torque generation section for attracting a magnetic member of the impeller and rotating the impeller, and a plurality of grooves for hydrodynamic bearing provided on an inner face of the housing on the impeller rotation torque generation section side. A side wall of each of the grooves for hydrodynamic bearing is formed as an inclined side wall inclined obliquely such that the groove for hydrodynamic bearing is expanded from a bottom face of the groove for hydrodynamic bearing toward an opening face of the groove for hydrodynamic bearing.

8 Claims, 14 Drawing Sheets

(51) Int. Cl.
*F04D 13/06* (2006.01)
*F04D 29/048* (2006.01)

(52) U.S. Cl.
CPC ............ *A61M1/1017* (2014.02); *F04D 13/06* (2013.01); *F04D 13/0666* (2013.01); *F04D 29/047* (2013.01); *F04D 29/048* (2013.01)

(56) References Cited

U.S. PATENT DOCUMENTS

| | | |
|---|---|---|
| 3,510,229 A | 5/1970 | Smith |
| 3,932,069 A | 1/1976 | Giardini et al. |
| 3,960,468 A | 6/1976 | Boorse et al. |
| 4,149,535 A | 4/1979 | Voider |
| 4,382,199 A | 5/1983 | Isaacson |
| 4,392,836 A | 7/1983 | Sugawara |
| 4,507,048 A | 3/1985 | Belenger et al. |
| 4,540,402 A | 9/1985 | Aigner |
| 4,549,860 A | 10/1985 | Yakich |
| 4,686,982 A | 8/1987 | Nash |
| 4,688,998 A | 8/1987 | Olsen et al. |
| 4,753,221 A | 6/1988 | Kensey et al. |
| 4,769,006 A | 9/1988 | Papantonakos |
| 4,790,843 A | 12/1988 | Carpentier et al. |
| 4,806,080 A | 2/1989 | Mizobuchi et al. |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Troup lin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,930,997 A | 6/1990 | Bennett |
| 4,944,722 A | 7/1990 | Carriker et al. |
| 4,957,504 A | 9/1990 | Chardack |
| 4,969,865 A | 11/1990 | Hwang et al. |
| 4,985,014 A | 1/1991 | Orejola |
| 4,995,857 A | 2/1991 | Arnold |
| 5,092,844 A | 3/1992 | Schwartz et al. |
| 5,092,879 A | 3/1992 | Jarvik |
| 5,106,263 A | 4/1992 | Irie |
| 5,106,273 A | 4/1992 | Lemarquand et al. |
| 5,106,372 A | 4/1992 | Ranford |
| 5,112,202 A | 5/1992 | Oshima et al. |
| 5,112,349 A | 5/1992 | Summers et al. |
| 5,129,883 A | 7/1992 | Black |
| 5,145,333 A | 9/1992 | Smith |
| 5,147,186 A | 9/1992 | Buckholtz |
| 5,190,528 A | 3/1993 | Fonger et al. |
| 5,201,679 A | 4/1993 | Velte et al. |
| 5,211,546 A | 5/1993 | Isaacson et al. |
| 5,275,580 A | 1/1994 | Yamazaki |
| 5,290,227 A | 3/1994 | Pasque |
| 5,290,236 A | 3/1994 | Mathewson |
| 5,306,295 A | 4/1994 | Kolff et al. |
| 5,312,341 A | 5/1994 | Turi |
| 5,332,374 A | 7/1994 | Kricker et al. |
| 5,346,458 A | 9/1994 | Afield |
| 5,350,283 A | 9/1994 | Nakazeki et al. |
| 5,354,331 A | 10/1994 | Schachar |
| 5,360,445 A | 11/1994 | Goldowsky |
| 5,370,509 A | 12/1994 | Golding et al. |
| 5,385,581 A | 1/1995 | Bramm et al. |
| 5,405,383 A | 4/1995 | Barr |
| 5,449,342 A | 9/1995 | Hirose et al. |
| 5,478,222 A | 12/1995 | Heidelberg et al. |
| 5,504,978 A | 4/1996 | Meyer, III |
| 5,507,629 A | 4/1996 | Jarvik |
| 5,533,957 A | 7/1996 | Aldea |
| 5,569,111 A | 10/1996 | Cho et al. |
| 5,575,630 A | 11/1996 | Nakazawa et al. |
| 5,595,762 A | 1/1997 | Derrieu et al. |
| 5,611,679 A | 3/1997 | Ghosh et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman, Jr. et al. |
| 5,695,471 A | 12/1997 | Wampler |
| 5,725,357 A | 3/1998 | Nakazeki et al. |
| 5,738,649 A | 4/1998 | Macoviak |
| 5,746,575 A | 5/1998 | Westphal et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,795,074 A | 8/1998 | Rahman et al. |
| 5,800,559 A | 9/1998 | Higham et al. |
| 5,807,311 A | 9/1998 | Palestrant |
| 5,814,011 A | 9/1998 | Corace |
| 5,824,069 A | 10/1998 | Lemole |
| 5,851,174 A | 12/1998 | Jarvik et al. |
| 5,853,394 A | 12/1998 | Tolkoff et al. |
| 5,868,702 A | 2/1999 | Stevens et al. |
| 5,868,703 A | 2/1999 | Bertolero et al. |
| 5,890,883 A | 4/1999 | Golding et al. |
| 5,924,848 A | 7/1999 | Izraelev |
| 5,924,975 A | 7/1999 | Goldowsky |
| 5,928,131 A | 7/1999 | Prem |
| 5,938,412 A | 8/1999 | Izraelev |
| 5,941,813 A | 8/1999 | Sievers et al. |
| 5,947,703 A | 9/1999 | Nojiri et al. |
| 5,951,263 A | 9/1999 | Taylor et al. |
| 5,964,694 A | 10/1999 | Siess et al. |
| 6,004,269 A | 12/1999 | Crowley et al. |
| 6,007,479 A | 12/1999 | Rottenberg et al. |
| 6,030,188 A | 2/2000 | Nojiri et al. |
| 6,042,347 A | 3/2000 | Scholl et al. |
| 6,053,705 A | 4/2000 | Schob et al. |
| 6,058,593 A | 5/2000 | Siess |
| 6,066,086 A | 5/2000 | Antaki et al. |
| 6,071,093 A | 6/2000 | Hart |
| 6,074,180 A | 6/2000 | Khanwilkar et al. |
| 6,080,133 A | 6/2000 | Wampler |
| 6,082,900 A * | 7/2000 | Takeuchi et al. ............... 384/115 |
| 6,086,527 A | 7/2000 | Talpade |
| 6,100,618 A | 8/2000 | Schoeb et al. |
| 6,123,659 A | 9/2000 | leBlanc et al. |
| 6,123,726 A | 9/2000 | Mori et al. |
| 6,139,487 A | 10/2000 | Siess |
| 6,142,752 A | 11/2000 | Akamatsu et al. |
| 6,143,025 A | 11/2000 | Stobie et al. |
| 6,146,325 A | 11/2000 | Lewis et al. |
| 6,149,683 A | 11/2000 | Lancisi et al. |
| 6,158,984 A | 12/2000 | Cao et al. |
| 6,171,078 B1 | 1/2001 | Schob |
| 6,176,822 B1 | 1/2001 | Nix et al. |
| 6,176,848 B1 | 1/2001 | Rau et al. |
| 6,190,304 B1 | 2/2001 | Downey et al. |
| 6,206,659 B1 | 3/2001 | Izraelev |
| 6,227,797 B1 | 5/2001 | Watterson et al. |
| 6,227,820 B1 | 5/2001 | Jarvik |
| 6,234,772 B1 | 5/2001 | Wampler et al. |
| 6,234,998 B1 | 5/2001 | Wampler |
| 6,245,007 B1 | 6/2001 | Bedingham et al. |
| 6,247,892 B1 | 6/2001 | Kazatchkov et al. |
| 6,254,359 B1 | 7/2001 | Aber |
| 6,264,635 B1 | 7/2001 | Wampler et al. |
| 6,293,901 B1 | 9/2001 | Prem |
| 6,295,877 B1 | 10/2001 | Aboul-Hosn et al. |
| 6,319,231 B1 | 11/2001 | Andrulitis |
| 6,351,048 B1 | 2/2002 | Schob et al. |
| 6,375,607 B1 | 4/2002 | Prem |
| 6,422,990 B1 | 7/2002 | Prem |
| 6,425,007 B1 | 7/2002 | Messinger |
| 6,428,464 B1 | 8/2002 | Bolling |
| 6,439,845 B1 | 8/2002 | Veres |
| 6,447,266 B2 | 9/2002 | Antaki et al. |
| 6,447,441 B1 | 9/2002 | Yu et al. |
| 6,458,163 B1 | 10/2002 | Slemker et al. |
| 6,508,777 B1 | 1/2003 | Macoviak et al. |
| 6,508,787 B2 | 1/2003 | Erbel et al. |
| 6,532,964 B2 | 3/2003 | Aboul-Hosn et al. |
| 6,533,716 B1 | 3/2003 | Schmitz-Rode et al. |

(56) References Cited

U.S. PATENT DOCUMENTS

| | | |
|---|---|---|
| 6,544,216 B1 | 4/2003 | Sammler et al. |
| 6,547,519 B2 | 4/2003 | deBlanc et al. |
| 6,547,530 B2 | 4/2003 | Ozaki et al. |
| 6,595,762 B2 | 7/2003 | Khanwilkar et al. |
| 6,609,883 B2 | 8/2003 | Woodard et al. |
| 6,623,420 B2 | 9/2003 | Reich et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,698,097 B1* | 3/2004 | Miura et al. ............ 29/898.02 |
| 6,709,418 B1 | 3/2004 | Aboul-Hosn et al. |
| 6,716,189 B1 | 4/2004 | Jarvik et al. |
| 6,776,578 B2 | 8/2004 | Belady |
| 6,790,171 B1 | 9/2004 | Griindeman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,860,713 B2 | 3/2005 | Hoover |
| 6,926,662 B1 | 8/2005 | Aboul-Hosn et al. |
| 6,935,344 B1 | 8/2005 | Aboul-Hosn et al. |
| 6,942,672 B2 | 9/2005 | Heilman et al. |
| 6,949,066 B2 | 9/2005 | Beamson et al. |
| 6,974,436 B1 | 12/2005 | Aboul-Hosn et al. |
| 6,991,595 B2 | 1/2006 | Burke et al. |
| 7,010,954 B2 | 3/2006 | Siess et al. |
| 7,011,620 B1 | 3/2006 | Siess |
| 7,027,875 B2 | 4/2006 | Siess et al. |
| 7,048,681 B2 | 5/2006 | Tsubouchi et al. |
| 7,112,903 B1 | 9/2006 | Schob |
| 7,128,538 B2 | 10/2006 | Tsubouchi et al. |
| 7,156,802 B2 | 1/2007 | Woodard et al. |
| 7,160,243 B2 | 1/2007 | Medvedev |
| 7,172,551 B2 | 2/2007 | Leasure |
| 7,175,588 B2 | 2/2007 | Morello |
| 7,241,257 B1 | 7/2007 | Ainsworth et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,431,688 B2 | 10/2008 | Wampler et al. |
| 7,467,930 B2 | 12/2008 | Ozaki et al. |
| 7,470,246 B2 | 12/2008 | Mori et al. |
| 7,491,163 B2 | 2/2009 | Viole et al. |
| 7,575,423 B2 | 8/2009 | Wampler |
| 7,645,225 B2 | 1/2010 | Medvedev et al. |
| 7,699,586 B2 | 4/2010 | LaRose et al. |
| 7,731,675 B2 | 6/2010 | Aboul-Hosn et al. |
| 7,748,964 B2 | 7/2010 | Yaegashi et al. |
| 7,802,966 B2 | 9/2010 | Wampler et al. |
| 7,841,976 B2 | 11/2010 | McBride et al. |
| 7,888,242 B2 | 2/2011 | Tanaka et al. |
| 7,934,909 B2 | 5/2011 | Nuesser et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,096,935 B2 | 1/2012 | Sutton et al. |
| 8,123,669 B2 | 2/2012 | Siess et al. |
| 8,226,373 B2 | 7/2012 | Yaehashi |
| 8,282,359 B2 | 10/2012 | Ayre et al. |
| 8,283,829 B2 | 10/2012 | Yamamoto et al. |
| 8,366,381 B2 | 2/2013 | Woodard et al. |
| 8,403,823 B2 | 3/2013 | Yu et al. |
| 8,512,012 B2 | 8/2013 | Akdis et al. |
| 2002/0058994 A1 | 5/2002 | Hill et al. |
| 2002/0095210 A1 | 7/2002 | Finnegan et al. |
| 2003/0023302 A1 | 1/2003 | Moe et al. |
| 2004/0007515 A1 | 1/2004 | Geyer |
| 2004/0024285 A1 | 2/2004 | Muckter |
| 2004/0030381 A1 | 2/2004 | Shu |
| 2004/0210305 A1 | 10/2004 | Shu et al. |
| 2005/0089422 A1 | 4/2005 | Ozaki et al. |
| 2005/0287022 A1* | 12/2005 | Yaegashi et al. ............ 417/420 |
| 2006/0024182 A1 | 2/2006 | Akdis et al. |
| 2006/0055274 A1 | 3/2006 | Kim |
| 2007/0078293 A1 | 4/2007 | Shambaugh, Jr. |
| 2007/0134993 A1 | 6/2007 | Tamez et al. |
| 2007/0213690 A1 | 9/2007 | Phillips et al. |
| 2007/0231135 A1 | 10/2007 | Wampler et al. |
| 2007/0297923 A1 | 12/2007 | Tada |
| 2008/0021394 A1 | 1/2008 | La Rose et al. |
| 2008/0030895 A1* | 2/2008 | Obara et al. ............ 360/99.08 |
| 2008/0124231 A1 | 5/2008 | Yaegashi |
| 2009/0060743 A1 | 3/2009 | McBride et al. |
| 2009/0074336 A1* | 3/2009 | Engesser et al. ............ 384/107 |
| 2009/0171136 A1 | 7/2009 | Shambaugh, Jr. |
| 2011/0118766 A1 | 5/2011 | Reichenbach et al. |
| 2011/0118829 A1 | 5/2011 | Hoarau et al. |
| 2011/0129373 A1 | 6/2011 | Mori |
| 2011/0243759 A1 | 10/2011 | Ozaki et al. |
| 2011/0318203 A1 | 12/2011 | Ozaki et al. |
| 2012/0003108 A1 | 1/2012 | Ozaki et al. |
| 2012/0016178 A1 | 1/2012 | Woodard et al. |
| 2012/0035411 A1 | 2/2012 | LaRose et al. |
| 2012/0078030 A1 | 3/2012 | Bourque |
| 2012/0130152 A1 | 5/2012 | Ozaki et al. |
| 2012/0243759 A1 | 9/2012 | Fujisawa |
| 2012/0308363 A1 | 12/2012 | Ozaki et al. |
| 2013/0121821 A1 | 5/2013 | Ozaki et al. |
| 2013/0170970 A1 | 7/2013 | Ozaki et al. |
| 2013/0178694 A1 | 7/2013 | Jeffery et al. |
| 2014/0030122 A1 | 1/2014 | Ozaki et al. |
| 2015/0017030 A1 | 1/2015 | Ozaki |

FOREIGN PATENT DOCUMENTS

| | | |
|---|---|---|
| EP | 1113117 A2 | 7/2001 |
| EP | 1495773 A2 | 1/2005 |
| EP | 1495773 A3 | 11/2006 |
| EP | 1495773 B1 | 2/2009 |
| EP | 2372160 A1 | 10/2011 |
| EP | 2405140 A1 | 1/2012 |
| EP | 2461465 A1 | 6/2012 |
| JP | 58/9535 | 1/1983 |
| JP | 61/293146 | 12/1986 |
| JP | 4-91396 A | 3/1992 |
| JP | 04/148094 A | 5/1992 |
| JP | 05/021197 U | 3/1993 |
| JP | 06/014538 U | 2/1994 |
| JP | 06/053790 U | 7/1994 |
| JP | 2006/070476 | 9/1994 |
| JP | 2006/245455 | 9/1994 |
| JP | 7-14220 U | 3/1995 |
| JP | 07/042869 U | 8/1995 |
| JP | 7-509156 A | 10/1995 |
| JP | 09/122228 A | 5/1997 |
| JP | 10/331841 A | 12/1998 |
| JP | 11/244377 A | 9/1999 |
| JP | 2001/309628 | 11/2001 |
| JP | 2003/135592 A | 5/2003 |
| JP | 2004/166401 A | 6/2004 |
| JP | 2004-209240 A | 7/2004 |
| JP | 2004/332566 A | 11/2004 |
| JP | 2004/346925 A | 12/2004 |
| JP | 2005/94955 | 4/2005 |
| JP | 2005/127222 A | 5/2005 |
| JP | 2005/245138 | 9/2005 |
| JP | 2005-270345 A | 10/2005 |
| JP | 2005-270415 A | 10/2005 |
| JP | 2005/287599 A | 10/2005 |
| JP | 2006/167173 A | 6/2006 |
| JP | 2007/002885 A | 1/2007 |
| JP | 2007/043821 | 2/2007 |
| JP | 2007/089972 A | 4/2007 |
| JP | 2007/089974 | 4/2007 |
| JP | 2007/215292 | 8/2007 |
| JP | 2007/247489 | 9/2007 |
| JP | 2008/011611 | 1/2008 |
| JP | 2008/104278 | 5/2008 |
| JP | 2008/132131 | 6/2008 |
| JP | 2008/99453 | 8/2008 |
| JP | 2008/193838 | 8/2008 |
| JP | 2008/297997 A | 12/2008 |
| JP | 2008/301634 | 12/2008 |
| JP | 2006/254619 | 9/2009 |
| JP | 2010/136863 A | 6/2010 |

(56) References Cited

FOREIGN PATENT DOCUMENTS

| JP | 2012/021413 | | 2/2012 |
|---|---|---|---|
| WO | 93/07388 | A1 | 4/1993 |
| WO | 96/31934 | | 10/1996 |
| WO | 97/42413 | A1 | 11/1997 |
| WO | 2005/028000 | A1 | 3/2005 |
| WO | 2005/034312 | A2 | 4/2005 |
| WO | 2009/157408 | A1 | 12/2009 |
| WO | 2010/067682 | A1 | 6/2010 |
| WO | 2010/101082 | A1 | 9/2010 |
| WO | 2011/013483 | A1 | 2/2011 |

OTHER PUBLICATIONS

Asama, et al., "Suspension Performance of a Two-Axis Actively Regulated Consequent-Pole Bearingless Motor," IEEE Transactions on Energy Conversion, vol. 28, No. 4, Dec. 2013, 8 pages.
European Search report Issued in European Patent Application No. 10/748,702.7, mailed Apr. 2, 2013.
Extended European Search Report issued in European Patent Application No. EP 10748677.1, mailed Nov. 19, 2012.
International Search Report (PCT/ISA/210) issued on Jul. 14, 2009, by Japanese Patent Office as the International Searching Authority for International Application No. PCT/JP2009/061318.
International Search Report and Written Opinion issued in PCT/JP2011/050925, mailed Apr. 12, 2011.
International Search Report and Written Opinion issued in PCT/JP2011/064768, mailed Sep. 13, 2011.
International Search Report and Written Opinion issued in PCT/JP2011/070450, mailed Dec. 13, 2011.
Kosaka, et al.,"Operating Point Control System for a Continuous Flow Artificial Heart: In Vitro Study," ASAIO Journal 2003, 6 pages.
Supplementary European Search Report issued in European Application No. 09/831,788.6, dated Jan. 7, 2013, 7 pages.
Terumo Heart, Inc., "Handled With Care—Significantly Reduce the Risk of Cell Damage," Terumo brochure, Apr. 2010, 2 pages.
Yamazaki, et al., "Development of a Miniature Intraventricular Axial Flow Blood Pump," ASAIO Journal, 1993, 7 pages.
International Search Report and Written Opinion of PCT/US2014/012448 mailed on Feb. 19, 2014, 8 pages.

\* cited by examiner

CENTRIFUGAL BLOOD PUMP DEVICE

CROSS REFERENCES TO RELATED APPLICATIONS

This application is a continuation of International Application No. PCT/JP2011/054134 filed on Feb. 24, 2011, and claims priority to Japanese Patent Application JP2010-071796 filed in the Japanese Patent Office on Mar. 26, 2010, the entire content of both of which is incorporated herein by reference.

TECHNICAL FIELD

This invention generally relates to a centrifugal blood pump device for sending blood.

BACKGROUND DISCUSSION

Recently, the situations in which a centrifugal blood pump is used for extracorporeal blood circulation in a pump-oxygenator is increasing. As a centrifugal pump, a pump of the type in which driving torque from an external motor is transmitted using magnetic coupling by completely eliminating physical communication between the external and a blood chamber in the pump to prevent invasion of bacteria and so forth is used.

An example of such a centrifugal blood pump as described above is a turbo type pump disclosed in Japanese Patent Laid-Open No. Hei 4-91396. This turbo type pump utilizes a magnetic coupling from a first permanent magnet disposed on one face of an impeller and a second permanent magnet disposed in an opposed relationship with the first permanent magnet with a housing interposed therebetween, and by rotating a rotor to which the second permanent magnet is attached, the impeller is driven to rotate. Then, although the impeller is attracted to the rotor side, since it has a groove for hydrodynamic bearing, the impeller is spaced, although only a little, away from the housing inner face by a hydrodynamic bearing effect formed between the groove for hydrodynamic bearing and the housing inner face and rotates in a non-contacting state.

Further, in the case of such a pump having hydrodynamic bearing as described above, the impeller for sending liquid is kept in a non-contacting relationship with a surrounding face by a load capacity (load capacity is a term for a bearing and has a dimension of force) generated by the groove for hydrodynamic bearing and a force counteracting the load capacity, for example, a magnetic force, thereby preventing hemolysis or formation of thrombus. Further, the load capacity varies depending upon the shape of the groove for hydrodynamic bearing. In other words, the shape design of the groove for hydrodynamic bearing is significant because this varies how great distance can be kept from the surroundings.

In a conventional hydrodynamic bearing, a logarithmic spiral shape is adopted as the shape of the groove for hydrodynamic bearing because it focuses on how the load capacity can be increased. However, in the case of a blood pump, not only is a high load capacity significant, but it is also significant that hemolysis is less likely to occur.

Therefore, the applicant of the present application proposed the pump described in U.S. Pat. No. 7,748,964 (Japanese Patent Laid-Open No. 2005-270345).

A centrifugal blood pump device 1 disclosed in this patent includes: an impeller 21 having a magnetic member 25 and rotating in a housing 20 to send blood; an impeller rotation torque generation section 3 for attracting and rotating the magnetic member 25 of the impeller 21; and grooves for hydrodynamic bearing 38 disposed on an inner face of the housing 20 on the impeller rotation torque generation section side. In each of the grooves for hydrodynamic bearing 38, a groove depth related value a (a=h1/h2), calculated from a distance h1 between the impeller 21 and the housing at a groove for hydrodynamic bearing portion upon rotation of the impeller and a distance h2 between the impeller and the housing at a groove for hydrodynamic bearing non-existing portion, satisfies 1.5 to 2.5, and a groove width related value s (s=Bo/B), calculated from a width Bo of a circumferential edge portion of the groove for hydrodynamic bearing and the sum B (B=Bo+B1) of the width Bo and a groove for hydrodynamic bearing non-existing portion width B1 between circumferential edges of adjacent ones of the grooves for hydrodynamic bearing, satisfies 0.6 to 0.8.

The applicant of the present application also proposed, in U.S. Pat. No. 7,470,246 (Japanese Patent Laid-Open No. 2004-209240), to chamfer a groove for hydrodynamic bearing such that a portion of the groove for hydrodynamic bearing which forms an angle has an R of at least 0.05 mm or more.

Hemolysis is less likely to occur in the case of the blood pumps described in U.S. Pat. No. 7,748,964 and U.S. Pat. No. 7,470,246, but further investigative efforts have led to the discovery of blood pumps able to inhibit or prevent hemolysis with a higher degree of certainty.

SUMMARY

A centrifugal blood pump device includes a housing having a blood inflow port and a blood outflow port, a centrifugal pump section including a magnetic member and a rotatable impeller which rotates in the housing to send blood by centrifugal force upon rotation, an impeller rotation torque generation section for attracting and rotating the impeller of the centrifugal pump section, and a plurality of grooves for hydrodynamic bearing disposed on a housing inner face on the impeller rotation torque generation section side or on a face of the impeller on the impeller rotation torque generation section side, with each of the grooves for hydrodynamic bearing opening to an opening face and possessing a bottom face. The impeller is rotatable in a non-contacting state with respect to the housing by the grooves for hydrodynamic bearing, and each of the grooves for hydrodynamic bearing has an inclined side wall inclined obliquely such that the groove for hydrodynamic bearing expands toward the opening face of the groove for hydrodynamic bearing from the bottom face of the groove for hydrodynamic bearing or from a location spaced a predetermined distance from the bottom face toward the opening face of the groove for hydrodynamic bearing.

A centrifugal blood pump device according to another aspect includes a housing possessing a blood inflow port opening to outside the housing and a blood outflow port opening to outside the housing, a blood chamber inside the housing in fluid communication with the blood inflow port and the blood outflow port, a rotatable impeller positioned in the blood chamber and rotatable in the blood chamber to send blood, which has entered the blood chamber from the blood inflow port, by centrifugal force to the blood outflow port, a magnetic member fixed to the impeller so that the magnetic member rotates together with the impeller, an impeller rotation torque generation section positioned on one axial end of the impeller to attract and rotate the impeller positioned in the blood chamber, and a plurality of grooves for hydrodynamic bearing. Each of the grooves for hydrodynamic bearing possessing a bottom face and an opening face at which the groove for hydrodynamic bearing opens. The grooves for hydrodynamic bearing are disposed either on an inner face of the housing which faces toward the impeller or on a face of the impeller which faces toward the impeller rotation torque generation section. The grooves for hydrodynamic bearing are configured to permit rotation of the impeller in a non-contacting state with respect to the housing, and each of the grooves for hydrodynamic bearing is defined by a side wall extending from the bottom face to the opening face of the groove. At least a part of the sidewall extending from the bottom face to the opening face is obliquely inclined so that the groove for hydrodynamic bearing expands outwardly toward the opening face of the groove for hydrodynamic bearing.

The centrifugal blood pump disclosed here is of the magnetically floating type in which a so-called groove for hydrodynamic bearing is utilized to rotate the impeller in a substantially non-contacting state with the housing so that the occurrence of hemolysis upon use is significantly diminished. With the blood pump device disclosed here by way of several examples, since the side wall of each of the grooves for hydrodynamic bearing is formed as an inclined face or surface, it is possible to reduce the shear stress at a groove for hydrodynamic bearing edge portion and hemolysis can be suppressed. Further, since the side wall of the groove for hydrodynamic bearing formation region is formed as an inclined face of surface, blood circulation between the inside and the outside of the grooves for hydrodynamic bearing is improved, and retention of blood can be prevented and thrombus formation in the inside of the grooves for hydrodynamic bearing is suppressed.

DETAILED DESCRIPTION

Figure 1:
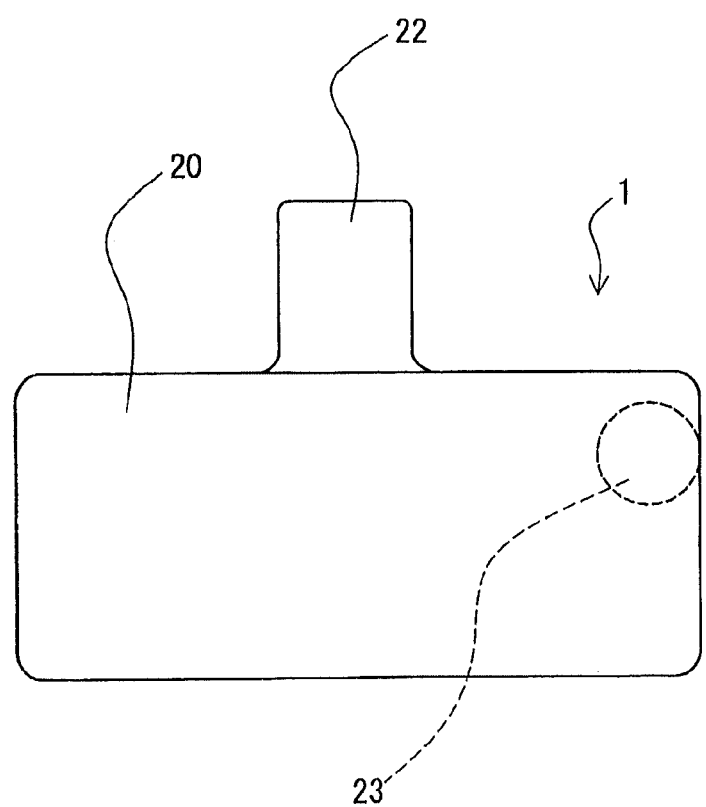
FIG. 1 is a front view of an embodiment of a centrifugal blood pump device constituting one example of the centrifugal blood pump disclosed here.

A centrifugal blood pump device 1 described below and illustrated in the drawing figures as an example of the centrifugal blood pump device disclosed here generally includes: a housing 20 having a blood inflow port 22 and a blood outflow port 23; a centrifugal pump section 2 including a magnetic member (in the present embodiment, a permanent magnet) 25, rotating in the housing 20, and having an impeller 21 for sending blood by utilizing centrifugal force upon rotation; an impeller rotation torque generation section 3 for attracting the magnetic member 25 of the impeller 21 of the centrifugal pump section 2 and rotating the impeller 21; and a plurality of grooves for hydrodynamic bearing 38 disposed on an inner face of the housing 20 on the impeller rotation torque generation section 3 side or on a face of the impeller 21 on the impeller rotation torque generation section side. In the centrifugal blood pump device 1, the impeller 21 is rotated in a non-contacting state with respect to the housing 20 by the grooves for hydrodynamic bearing 38. Further, each of the grooves for hydrodynamic bearing 38 has inclined side faces which are inclined obliquely such that the groove for hydrodynamic bearing (the width of the groove for hydrodynamic bearing) expands toward an opening face of the groove for hydrodynamic bearing 38 from a bottom face 53 of the groove for hydrodynamic bearing 38 or from a portion of a predetermined length of the opening face from the bottom face 53. In the centrifugal blood pump device of the embodiment shown, a side wall 52 of the groove for hydrodynamic bearing 38 is formed as an inclined side wall 52 which is inclined obliquely such that the groove for hydrodynamic bearing expands from the bottom face 53 of the groove for hydrodynamic bearing 38 toward the opening face (in other words, an upper face) of the groove for hydrodynamic bearing 38.

As shown in FIGS. 1 to 5, the centrifugal blood pump device 1 of the present embodiment includes, in more detail, the housing 20 having the blood inflow port 22 and the blood outflow port 23, a centrifugal blood pump section 2 having the impeller 21 rotatable in the housing 20 to send blood by centrifugal force upon rotation, and the impeller rotation torque generation section 3 for the impeller 21.

Further, in the centrifugal blood pump device 1 of the present embodiment, the impeller rotation torque generation section 3 includes a rotor 31 having a magnet 33 for attracting the magnetic member 25 of the impeller 21, and a motor 34 for rotating the rotor 31.

Further, the centrifugal blood pump device 1 of the present embodiment includes an impeller auxiliary attracting section 4 for attracting the impeller 21 in an opposite direction to the impeller rotation torque generation section 3. The impeller auxiliary attracting section 4 is an example of a floating assisting mechanism that magnetically attracts the second magnetic member of the impeller to a side opposite the impeller rotation torque generation section to assist floating of the impeller 21 in the housing 20.

The impeller 21 rotates without contacting the housing inner surface because of pressure generated by the groove for hydrodynamic bearing 38 upon rotation. Particularly in the present pump device 1, since the impeller 21 is attracted in the opposite direction to the rotor by a permanent magnet 41, the rotation is carried out in a state in which it is spaced by a distance greater than an ordinary distance between the impeller and the housing obtained by the groove for hydrodynamic bearing.

Figure 2:
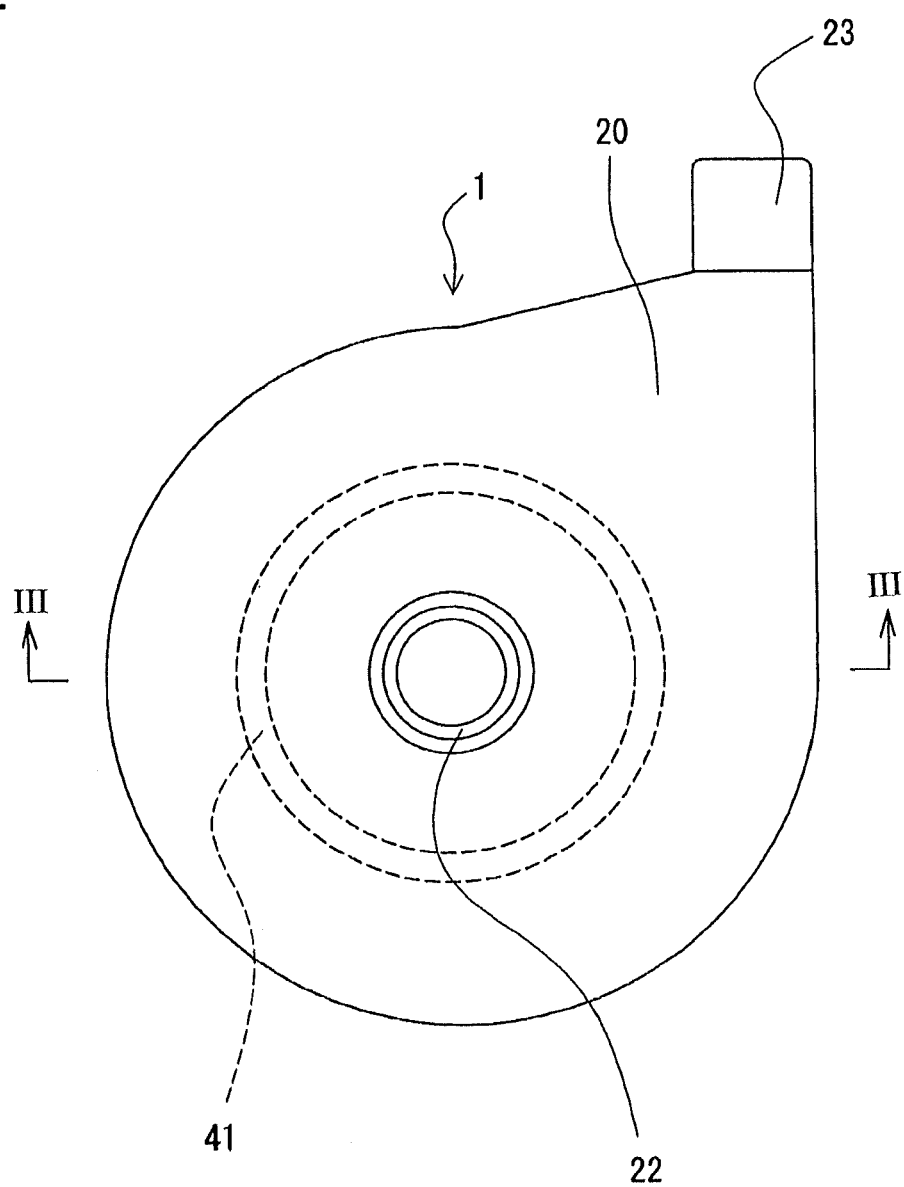
FIG. 2 is a plan view of the centrifugal blood pump device shown in FIG. 1.
Figure 4:
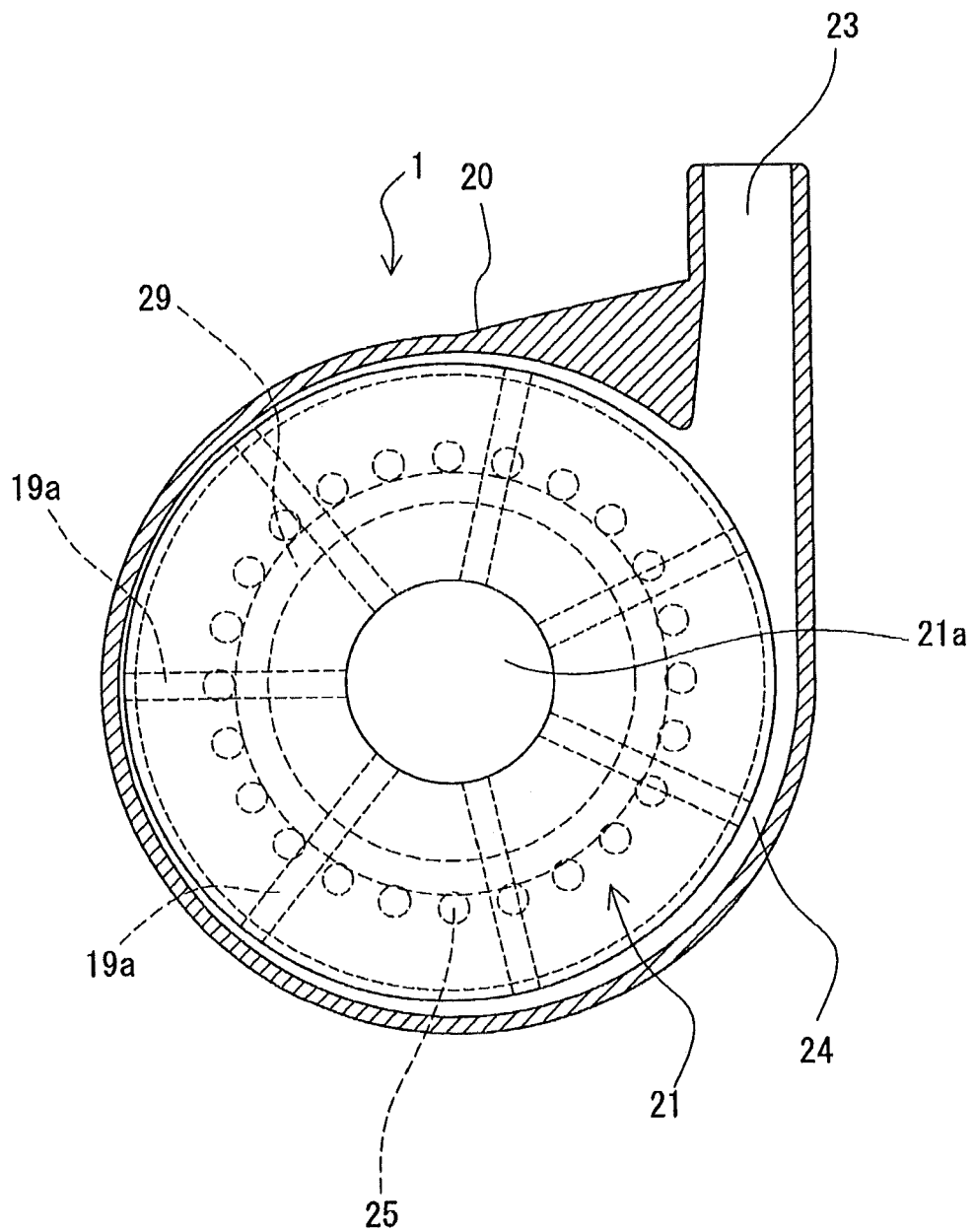
FIG. 4 is a cross-sectional view taken along the section line IV-IV in FIG. 3, with the outer appearance of the impeller being represented.
Figure 5:
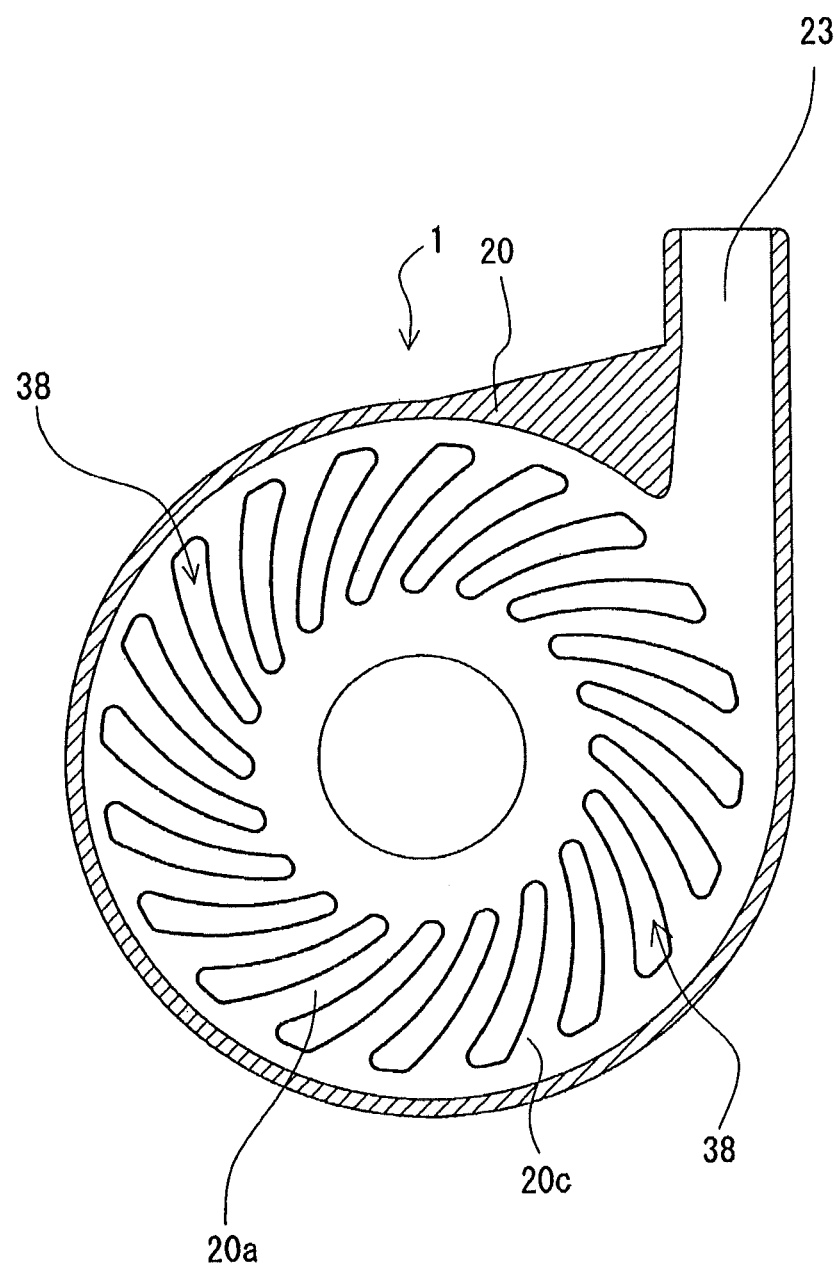
FIG. 5 is a cross-sectional view illustrating a state in which the impeller is removed from the cross-sectional view taken along the section line IV-IV in FIG. 3.
Figure 8:
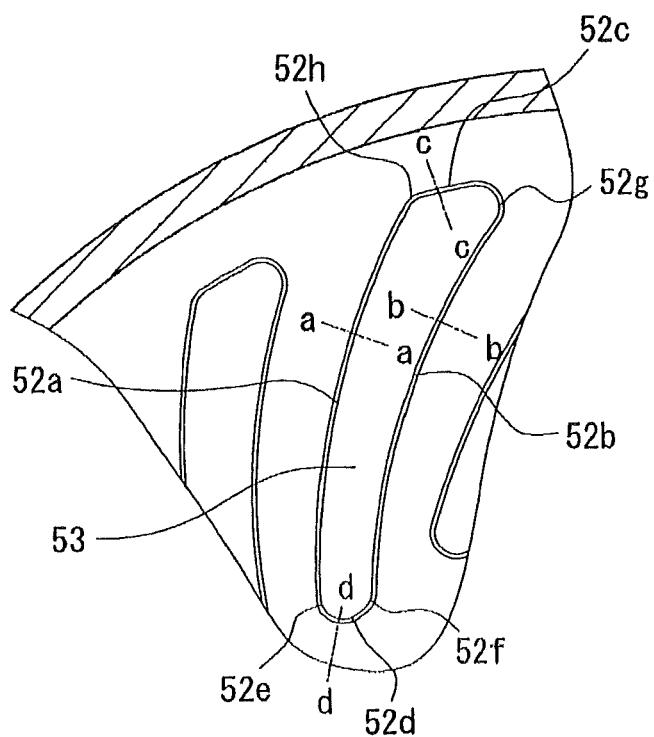
FIG. 8 is an explanatory view illustrating a form of a groove for hydrodynamic bearing in the example of the centrifugal blood pump device disclosed here.

The housing 20 has the blood inflow port 22 and the blood outflow port 23 and is formed from a nonmagnetic material. In the housing 20, a blood chamber 24 is formed in a communicating relationship with the blood inflow port 22 and the blood outflow port 23. In this housing 20, the impeller 21 is accommodated. The blood inflow port 22 is provided such that it projects substantially perpendicularly from a portion in the proximity of the center or center portion of an upper face of the housing 20. It is to be noted that the blood inflow port 22 is not limited to the illustrated straight pipe, but may be a curved pipe or a bent pipe. The blood outflow port 23 is provided such that it projects in a tangential direction from a side face of the housing 20 which is substantially cylindrically-shaped as shown in FIGS. 2 and 4. As shown in FIG. 4, the impeller 21 is disk-shaped, has a through hole 21a at its center and is accommodated in the blood chamber 24 located in the housing 20. The housing 20 in the present embodiment does not substantially include a volute. Therefore, the blood outflow port directly communicates with part of an impeller rotation region 20c of the centrifugal pump section 2 as shown in FIGS. 5 and 8. Further, the blood outflow port 23 extends linearly and parallel to a tangential direction of the impeller rotation region 20c.

Figure 3:
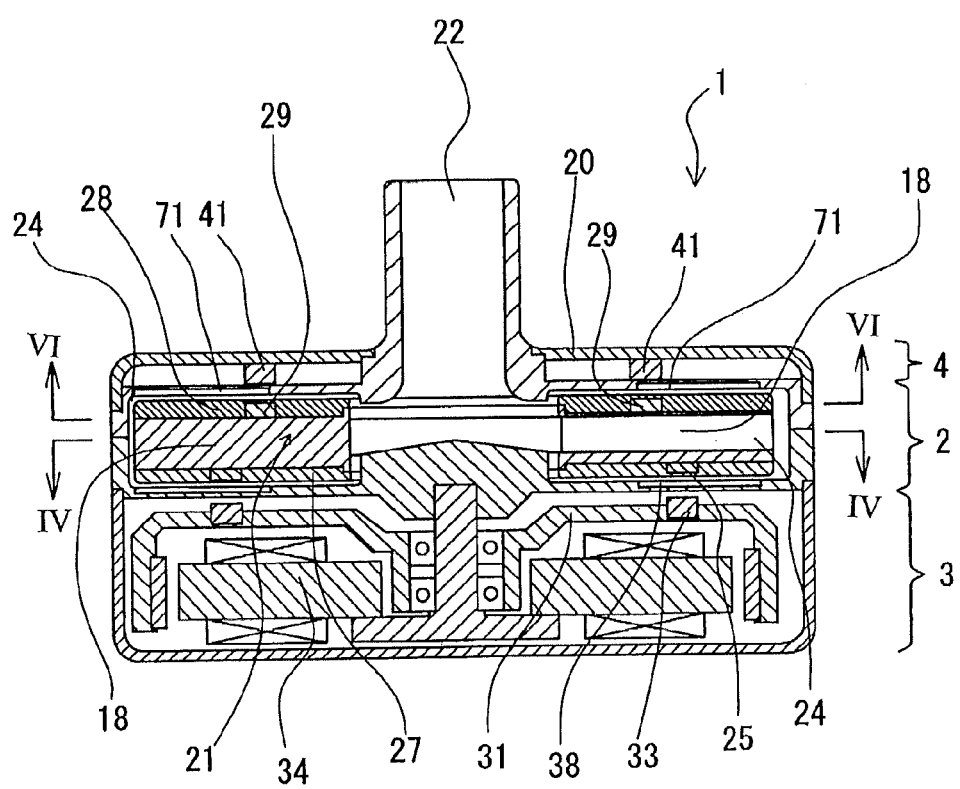
FIG. 3 is a cross-sectional view taken along a line in FIG. 2.

The impeller 21 includes a ring-shaped impeller main body member 18, and a ring-shaped impeller surface formation member 28 secured to one of the faces of the impeller main body member 18 as shown in FIG. 3. The impeller 21 in the present embodiment includes a second ring-shaped impeller surface formation member 27 secured to the other face of the impeller main body member 18.

Figure 7:
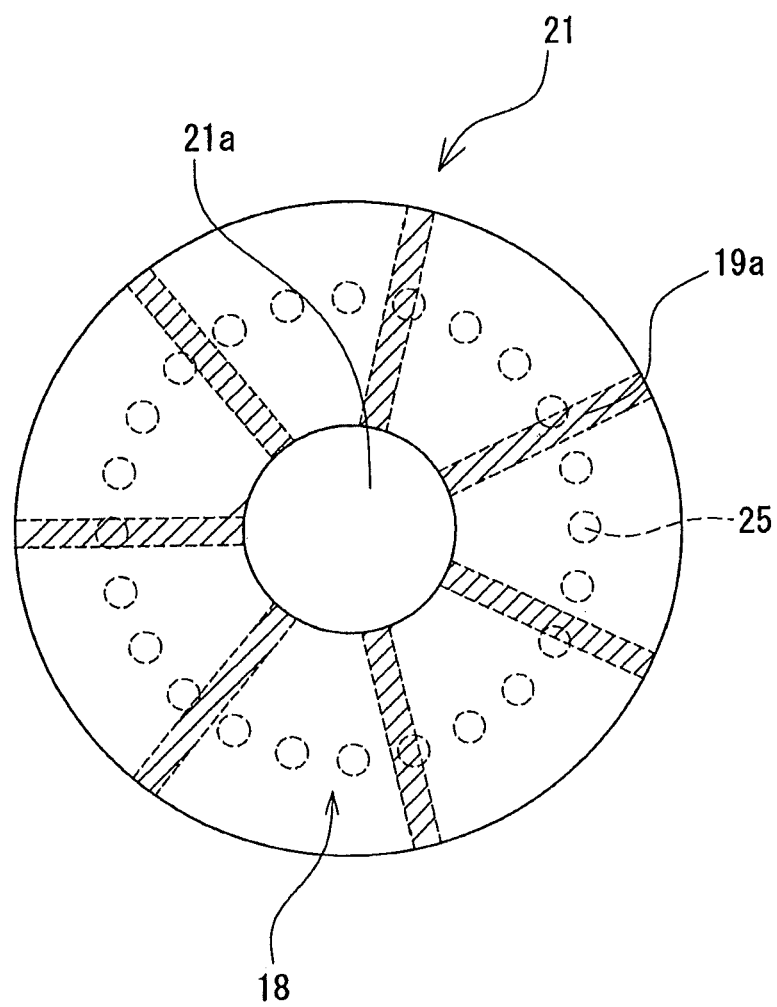
FIG. 7 is a cross-sectional view of the impeller in the centrifugal blood pump device of FIG. 4.

Further, as shown in FIGS. 4 and 7, the impeller main body member 18 includes a plurality of (in the present embodiment, seven) vane formation portions 19a disposed at equal angular intervals so that equal spacing exists between circumferentially adjacent vanes, an upper ring portion which interconnects upper portions of the plural vane formation portions 19a, and a lower ring portion which interconnects lower portions of the plural vane formation portions 19a.

The impeller surface formation member 28 is a ring-shaped member and includes an accommodation section for accommodating or receiving a second magnetic member 29, and the second magnetic member 29 is disposed immovably between the impeller main body member 18 and the impeller surface formation member 28. It is to be noted that the second magnetic member accommodation section may be disposed in the impeller main body member 18 or may be disposed in a distributed state in both of the impeller surface formation member 28 and the impeller main body member 18.

The second impeller surface formation member 27 is a ring-shaped member. The impeller surface formation member 27 includes an accommodation section for the first magnetic member 25, and the first magnetic member 25 is disposed immovably between the impeller main body member 18 and the second impeller surface formation member 27. It is to be noted that the first magnetic member accommodation section may be disposed in the impeller main body member 18 or may be disposed in a distributed state in both of the second impeller surface formation member 27 and the impeller main body member 18.

The impeller main body member 18, impeller surface formation member 28 and second impeller surface formation member 27 are formed from a nonmagnetic material.

For the second magnetic member 29, magnetic stainless steel, a permanent magnet or the like is used. In the present embodiment, the second magnetic member 29 is ring-shaped so as to correspond to the shape of the permanent magnet 41 as shown in FIG. 4. It is to be noted that the second magnetic member 29 may be configured by disposing a plurality of magnetic members at equal angles.

The first magnetic member 25 is formed using a permanent magnet, magnetic stainless steel or the like and particularly preferably using a permanent magnet. In the present embodiment, the impeller 21 has a plurality of (for example, 14 to 24) first magnetic members 25 (permanent magnets, follower magnets) embedded therein. The first magnetic members 25 (permanent magnets) are provided such that they attract the impeller 21 to the opposite side to the blood inflow port 22 by the permanent magnets 33 disposed on the rotor 31 of the impeller rotation torque generation section 3 so that magnetic coupling force with the rotor and rotation torque are transmitted from the impeller rotation torque generation section 3. Embedding a certain number of magnetic members 25 as in the present embodiment, helps achieve sufficient magnetic coupling to the rotor 31.

Further, the impeller 21 has a plurality of (seven) blood paths as seen in FIG. 7, each of which is partitioned or bordered by adjacent ones of the vane formation portions 19a. As shown in FIG. 7, the blood paths communicate with a center opening of the impeller 21 and extend such that the width of the blood paths gradually increases from a start portion at the center opening of the impeller 21 to an outer circumferential edge. The vane formation portions 19a are thus formed between adjacent ones of the blood paths. It is to be noted that, in the present embodiment, the blood paths and the vane formation portions 19a are respectively formed at equal angular distances and in a substantially common shape.

As shown in FIG. 3, the impeller rotation torque generation section 3 includes the rotor 31 accommodated in the housing 20, and the motor 34 for rotating the rotor 31. The rotor 31 includes the plurality of permanent magnets 33 disposed on a face thereof on the blood pump section 2 side. The rotor 31 is fixed at the center thereof to a rotary shaft of the motor 34. The plurality of permanent magnets 33 are disposed at equal angles so as to correspond to the arrangement form (number and arrangement positions) of the first magnetic members (permanent magnets) 25 of the impeller 21. Further, as a motor for driving the rotor 31 to rotate, a synchronous motor including a DC brushless motor, an asynchronous motor including an induction motor, or the like is used. However, the type of the motor may be any type. The center of the plural permanent magnets 33 and the center of the rotor when the motor is rotating coincide with each other.

The impeller auxiliary attracting section 4 includes at least one permanent magnet 41 secured thereto to attract the second magnetic member 29 of the impeller as shown in FIGS. 2 and 3. In particular, as the permanent magnet 41, a ring-shaped permanent magnet is used. Further, a plurality of ring-shaped permanent magnets may be disposed concentrically. Furthermore, the permanent magnet 41 may be formed from a plurality of permanent magnets disposed at equal angular distances. In this instance, the number of permanent magnets preferably is 2 to 8, and particularly preferably is 3 to 6.

Although the permanent magnet 41 is used in the present embodiment, the magnetic member for attracting the second magnetic member 29 to the opposite side to the attraction direction of the impeller rotation torque generation section may be an electromagnet. Further, a ferromagnetic member is also possible if the second magnetic member is a permanent magnet.

The centrifugal blood pump device of the present embodiment also includes a groove for hydrodynamic bearing formation region provided on the inner face of the housing 20 on the impeller side. A plurality of grooves for hydrodynamic bearing 38 are provided in the groove for hydrodynamic bearing formation region. The grooves for hydrodynamic bearing 38 are provided either on the inner face of a portion of the housing 20 that faces the impeller 21 and that is positioned between the impeller 21 and the rotor 31 or on a face of the impeller which faces in a direction toward the rotor 3. Further, the side wall 52 of each groove for hydrodynamic bearing 38 is formed as an inclined side wall 52 which is inclined obliquely such that the groove for hydrodynamic bearing expands toward the upper face of the groove for hydrodynamic bearing 38 from the bottom face 53 of the groove for hydrodynamic bearing 38.

As shown in FIG. 5, the groove for hydrodynamic bearing 38 is formed in a size corresponding to the bottom face (rotor side face) of the impeller 21. In the pump device 1 of the present embodiment, the groove for hydrodynamic bearing 38 has one end (inner end) on a circumferential edge (circumference) of a circular portion spaced slightly outwardly from the center of the housing inner face 20a and extends spirally (in other words, in a curved state) such that the width of the groove for hydrodynamic bearing 38 gradually increases to a location in the proximity of an outer edge of the housing inner face 20a. Further, a plurality of such groove for hydrodynamic bearings 38 are provided, and all of the grooves for hydrodynamic bearing 38 have substantially the same shape and are disposed substantially at equal distances. Each groove for hydrodynamic bearing 38 is a concave portion and preferably has a depth of approximately 0.01 to 0.4 mm. The number of such grooves for hydrodynamic bearing preferably is 6 to 36, and particularly preferably is approximately 8 to 24. In the present embodiment, twenty grooves for hydrodynamic bearing are disposed at equal angles with respect to the center axis of the impeller.

The grooves for hydrodynamic bearing may be provided on the face of the impeller 21 so that they are not on the housing side but are on the rotor side. Also in this instance, the grooves for hydrodynamic bearing preferably have a configuration similar to that of the grooves for hydrodynamic bearing described hereinabove.

As shown in FIG. 8, each of the grooves for hydrodynamic bearing 38 formed at the groove for hydrodynamic bearing formation region has a first longer side 52a and a second longer side 52b extending from a peripheral edge of the groove for hydrodynamic bearing formation region toward the center and opposing each other, a first shorter side 52c interconnecting end portions of the first longer side 52a and the second longer side 52b on the outer peripheral edge side of the groove for hydrodynamic bearing formation region, and a second shorter side 52d interconnecting end portions of the first longer side 52a and the second longer side 52b on the center side of the groove for hydrodynamic bearing formation region.

In the present embodiment, the first longer side 52a and the second longer side 52b are arcuate longer sides curved in the same direction, and the first longer side 52a is positioned forwardly in the curved direction while the second longer side 52b is positioned rearwardly in the curved direction. Therefore, each groove for hydrodynamic bearing 38 is curved in a bow shape. The plural grooves for hydrodynamic bearing 38 are provided in such a manner as to surround the center of the groove for hydrodynamic bearing formation region. Further, each groove for hydrodynamic bearing 38 has a width which gradually increases from the center side to the peripheral edge side.

A connecting portion 52g between the second longer side 52b and the first shorter side 52c has an arcuate shape having a center point on the inner side of the connecting portion 52g and in the proximity of the connecting portion 52g. With this configuration, the retention of blood can be prevented with a higher degree of certainty, and also the fabrication is easier. Further, the second shorter side 52d is a curved side which is curved at a center portion thereof to the center side of the groove for hydrodynamic bearing formation region (curved so that the convex portion of the curved side projects toward the center side). This configuration also helps prevent the retention of blood with a higher degree of certainty and also the fabrication is easier.

Figure 9:
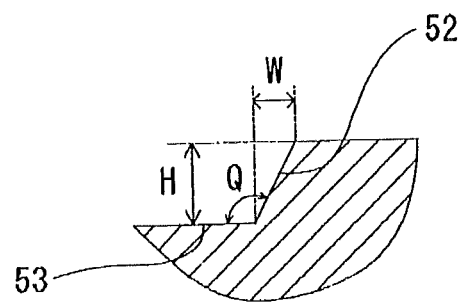
FIG. 9 is an explanatory view illustrating a cross-sectional form of the groove for hydrodynamic bearing at the section lines a-a, b-b, c-c and d-d shown in FIG. 8.

In the present embodiment, the side walls of the first longer side 52a, second longer side 52b, first shorter side 52c and second shorter side 52d of each groove for hydrodynamic bearing 38 are formed as inclined faces which are all inclined so as to be expanded upwardly (in a direction toward the impeller). In particular, a section of the first longer side 52a taken along a section line a-a, a section of the second longer side 52b taken along a line b-b, a section of the first shorter side 52c taken along a line c-c and a section of the second shorter side 52d taken along a line d-d in FIG. 8 are all inclined faces which are all inclined so as to expand upwardly (in a direction toward the impeller) as shown in FIG. 9.

As the gradient of the side faces, the relationship (W/H) between the width W of the inclined side faces and the groove for hydrodynamic bearing depth H preferably is 1/10 to 2, and particularly preferably is 5/10 to 1.5. Further, since the side wall of the first longer side portion 52a, the side wall of the second longer side portion 52b, the side wall of the first shorter side portion 52c and the side wall of the second shorter side portion 52d are all formed as inclined faces inclined in such a manner as to expand upwardly (in a direction toward the impeller) as described above, they form an obtuse angle θ with respect to the bottom face 53 of the groove for hydrodynamic bearing 38.

Since such grooves for hydrodynamic bearing as described above are provided, although the attraction to the impeller rotation torque generation section 3 side is carried out, a space is made, although only a little, away from the housing inner face by a hydrodynamic bearing effect formed between the groove for hydrodynamic bearing 38 of the housing and the bottom face of the impeller 21 (or between the grooves for hydrodynamic bearing of the impeller and the housing inner face), and the rotation is carried out in a non-contacting state. Consequently, a blood flow path is relatively assured between the lower face of the impeller and the housing inner face and blood circulation into the grooves for hydrodynamic bearing is enhanced. Therefore, blood retention and generation of a thrombus originating from the blood stagnation are prevented.

Further, in the present embodiment, the gradients of the side walls of the first longer side 52a, second longer side 52b, first shorter side 52c and second shorter side 52d of the groove for hydrodynamic bearing 38 are substantially equal to each other.

Figure 10:
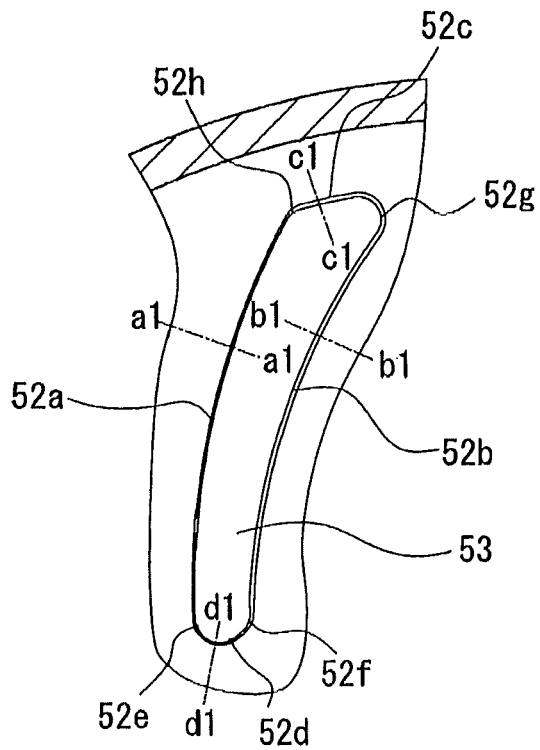
FIG. 10 is an explanatory view illustrating a form of a groove for hydrodynamic bearing in a centrifugal blood pump device of another embodiment.
Figure 11:
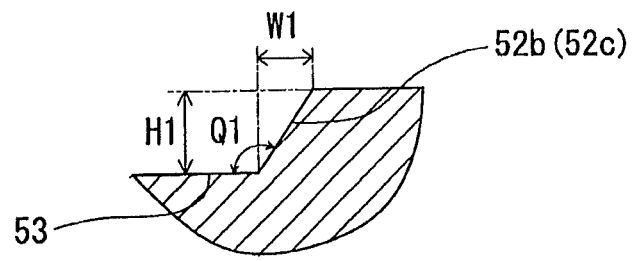
FIG. 11 is an explanatory view illustrating a cross-sectional form of the groove for hydrodynamic bearing shown in FIG. 10.
Figure 12:
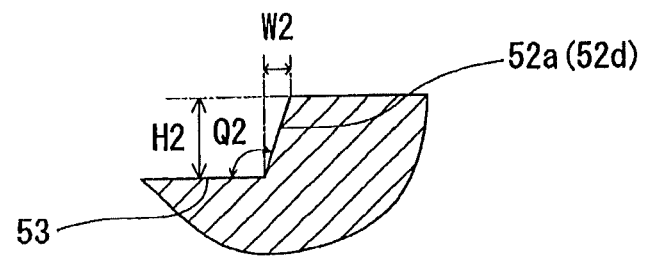
FIG. 12 is an explanatory view illustrating a cross-sectional form of the groove for hydrodynamic bearing shown in FIG. 10.

The gradients of the side walls of the first longer side 52a, second longer side 52b, first shorter side 52c and second shorter side 52*d* of the groove for hydrodynamic bearing 38 may not be equal to each other but be different from each other. For example, as shown in FIGS. 10, 11 and 12, the gradient of the side wall of the second longer side 52*b* (angle between the inclined face and the bottom face) may be greater than the gradient of the side wall of the first longer side 52*a* (angle between the inclined face and the bottom face). In particular, the section of the second longer side 52*b* taken along a section line b1-b1 may be formed such that the gradient (angle θ1 between the inclined face and the bottom face) is relatively greater as shown in FIG. 11, and the section of the first longer side 52*a* taken along a section line a1-a1 may be formed such that the angle thereof may be θ2 which is relatively smaller than the angle θ1 described above as shown in FIG. 12. By such a configuration as just described, the side face of the second longer side 52*b* positioned rearwardly in the curved direction of the groove for hydrodynamic bearing becomes a moderate inclined face and flowing of blood into the groove for hydrodynamic bearing 38 is enhanced, and the side face of the first longer side 52*b* positioned forwardly in the curved direction of the groove for hydrodynamic bearing becomes an inclined face which does not have a great inclination and dynamic pressure can be expressed with certainty. Further, the section of the first shorter side 52*c* taken along a section line c1-c1 may be formed such that the gradient (angle θ1 between the inclined face and the bottom face) is relatively greater as shown in FIG. 11, and the section of the second longer side 52*d* taken along a section line d1-d1 may be formed such that the angle thereof may be θ2 which is relatively smaller than the angle θ1 described above as shown in FIG. 12. By such a configuration as just described, the side face of the first shorter side 52*c* positioned on the outer circumference side of the groove for hydrodynamic bearing becomes a moderate inclined face and flowing of blood into the groove for hydrodynamic bearing 38 is enhanced.

Figure 18:
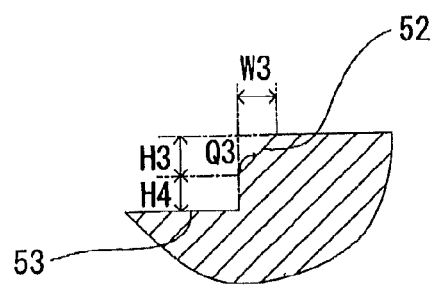
FIG. 18 is an explanatory view illustrating a cross-sectional form of a groove for hydrodynamic bearing of a centrifugal blood pump device of another embodiment.

In the embodiment described above, the entire side wall of each groove for hydrodynamic bearing 38 is formed as an inclined side wall. That is, the sidewall is inclined such that the groove for hydrodynamic bearing expands outwardly over its entire depth. Although this is preferable, the side wall is not limited to this configuration. As shown in FIG. 18, the groove for hydrodynamic bearing 38 may have an inclined side wall which is inclined obliquely such that the groove for hydrodynamic bearing begins expanding toward the opening face of the groove for hydrodynamic bearing 38 from a portion spaced a predetermined distance (a relatively small distance) from the bottom face 53 of the groove for hydrodynamic bearing 38 toward the opening face. In this embodiment, a part of the sidewall extending from the bottom face to the opening face is obliquely inclined to provide the groove for hydrodynamic bearing that expands outwardly toward the opening face of the groove for hydrodynamic bearing. The sidewall is thus inclined such that the groove for hydrodynamic bearing expands outwardly over only a portion of its entire depth.

In this instance, as the gradient of each inclined side wall portion, the relationship (W3/H3) between a width W3 of the inclined side wall portion and a depth H3 of the inclined side wall portion preferably is 1/10 to 2, and particularly preferably is 1/2 to 3/2. Further, the relationship (H4/(H3+H4)) between a distance H4 from the groove for hydrodynamic bearing bottom face to the starting portion of the inclined side wall portion and the groove for hydrodynamic bearing depth (H3+H4) preferably is 0 to 9/10, and particularly preferably is 0 to 4/5.

The groove for hydrodynamic bearing of the type as just described can be configured such that the gradients of the inclined side wall portions of the first longer side, second longer side, first shorter side and second shorter side may be substantially equal to each other, or the gradients of the inclined side wall portions of the side walls of the first longer side, second longer side, first shorter side and second shorter side may be different from each other similarly to those described hereinabove. By the configuration just described, the retention of blood can be prevented with a higher degree of certainty and also the fabrication is easier.

Figure 6:
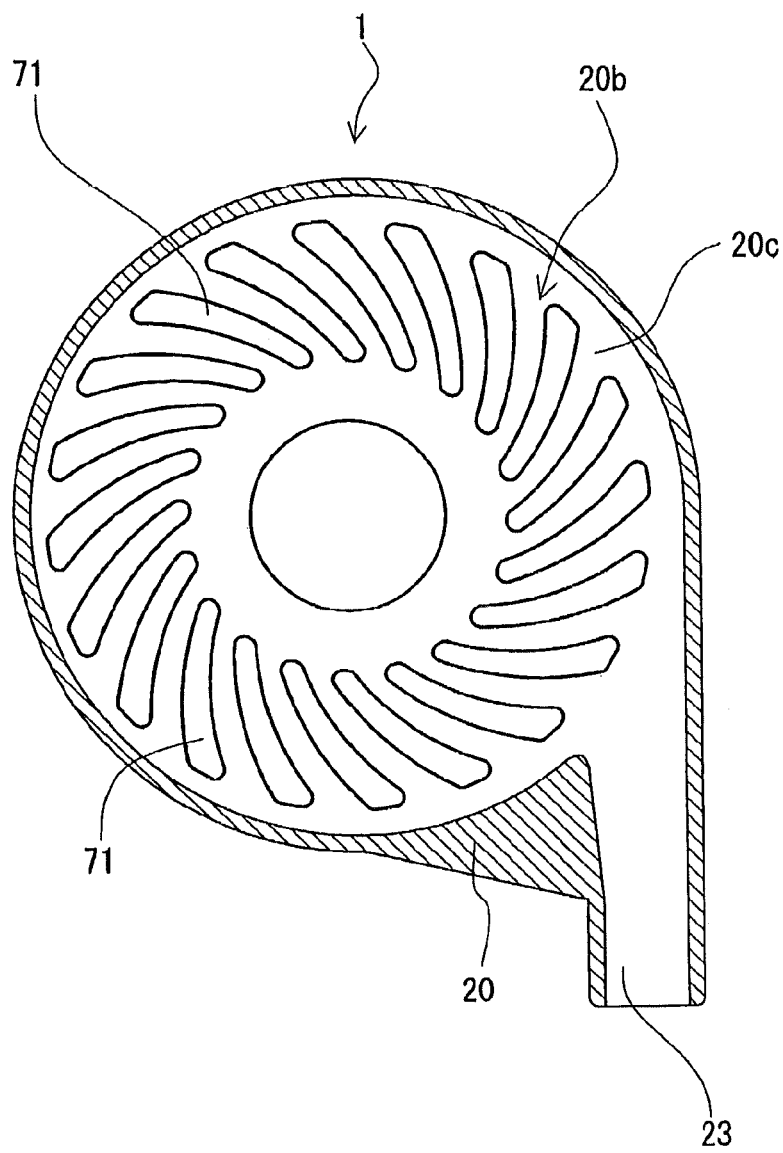
FIG. 6 is a cross-sectional view illustrating a state in which the impeller is removed from the FIG. 4 cross-sectional view.

The centrifugal blood pump device 1 of the present embodiment includes a floating assisting mechanism as mentioned above. As shown in FIG. 6, the housing 20 has floating assisting mechanism side grooves for hydrodynamic bearing (second grooves for hydrodynamic bearing) 71 disposed on a housing inner face 20*b* on the impeller auxiliary attracting section 4 side (floating assisting mechanism side, permanent magnet 41 side).

Therefore, the impeller 21 rotates in a non-contacting state by a hydrodynamic bearing effect formed between the first grooves for hydrodynamic bearing 38 and the impeller 21, and generated by rotation of the impeller 21 at a speed higher than a predetermined speed, and prevents, when an external impact is applied or when the dynamic pressure by the first grooves for hydrodynamic bearing 38 becomes excessively high, close contact of the impeller with the housing inner face 20*b* side. The dynamic pressure generated by the first grooves for hydrodynamic bearing and the dynamic pressure generated by the second grooves for hydrodynamic bearing may be different from each other.

The impeller 21 preferably rotates in a state in which the gap between the impeller surface formation member 28 of the impeller 21 and the housing inner face 20*b* and the gap between the second impeller surface formation member 27 of the impeller 21 and the housing inner face 20*a* are substantially equal to each other. If disturbance such as fluid force acting upon the impeller 21 is relatively great and one of the gaps is narrowed, the shapes of the grooves are preferably made different from each other in order that the dynamic pressure by the grooves for hydrodynamic bearing disposed on the narrowed side is made higher than the dynamic pressure by the other grooves for hydrodynamic bearing so that the two gaps may be substantially equal to each other. If the disturbance such as fluid force acting upon the impeller 21 is low, the shapes of the two grooves for hydrodynamic bearing are preferably same as each other.

The grooves for hydrodynamic bearing 71 are formed in a size corresponding to an upper face (auxiliary attraction side face) of the impeller 21 as shown in FIG. 6. That is, the grooves for hydrodynamic bearing 71 cover an area/region corresponding in size to the upper face of the impeller 21. In the pump device 1 of the present embodiment, each of the grooves for hydrodynamic bearing 71 has one end (inner end) on a circumferential edge (circumference) of a circular portion spaced a little outwardly from the center of the housing inner face 20*b* and extends spirally (in other words, in a curved stage) such that the width of each groove for hydrodynamic bearing 71 gradually increases toward the proximity of an outer edge of the housing inner face 20*b*. Further, a plurality of such grooves for hydrodynamic bearing 71 are provided, and the grooves for hydrodynamic bearing 71 respectively have substantially the same shape and are disposed at substantially equal distances. Each groove for hydrodynamic bearing 71 is a concave portion and preferably has a depth of approximately 0.01 to 0.4 mm. Approximately 6 to 36 grooves for hydrodynamic bearing are preferably provided, and particularly approximately 8 to 24 grooves for hydrodynamic bearing are preferably provided. In the present embodiment, 20 grooves for hydrodynamic bearing are disposed at equal angles with respect to the center axis of the impeller. It is to be noted that the grooves for hydrodynamic bearing 71 may be provided not on the housing side but on the face of the impeller 21 on the auxiliary attraction section side.

The grooves for hydrodynamic bearing 71 preferably have a form that is the same as that of the grooves for hydrodynamic bearing 38 described hereinabove except that they have a mirror-symmetrical (reversed) shape as seen in FIG. 6. The second grooves for hydrodynamic bearing 71 are also formed in a size corresponding to the upper face (auxiliary attraction section side face) of the impeller 21.

Each side wall of each groove for hydrodynamic bearing 71 is formed, as with the case of the groove for hydrodynamic bearing 38 described above, as an inclined side wall which is inclined obliquely such that the groove for hydrodynamic bearing expands from the bottom face of the groove for hydrodynamic bearing 71 toward the opening face (in other words, toward the lower face or open end) of the grooves for hydrodynamic bearing 71. Further, the shape of each groove for hydrodynamic bearing 71 preferably has a configuration the same as that described above with respect to the grooves for hydrodynamic bearing 38.

Each groove for hydrodynamic bearing 71 formed at the groove for hydrodynamic bearing formation region has, similarly to the groove for hydrodynamic bearing 38 described above, a first longer side and a second longer side extending from a circumferential outer edge toward the center side of the groove for hydrodynamic bearing formation region and opposed to each other, a first shorter side interconnecting end portions of the first longer side and the second longer side on the circumferential edge side of the groove for hydrodynamic bearing formation region, and a second shorter side interconnecting end portions of the first longer side and the second longer side on the center side of the groove for hydrodynamic bearing formation region.

Further, in the present embodiment, the first longer side and the second longer side are arcuate longer sides curved in the same direction, and the first longer side is positioned forwardly in the curved direction while the second longer side is positioned rearwardly in the curved direction. Therefore, each groove for hydrodynamic bearing 71 is curved in a bow shape. The plural grooves for hydrodynamic bearing are provided in such a manner as to surround the center of the groove for hydrodynamic bearing formation region. Each groove for hydrodynamic bearing has a width which gradually increases from the center side to the peripheral edge side.

In the present embodiment, a connecting portion between the second longer side and the first shorter side is arc-shaped having a center point on the inner side of the connecting portion and in the proximity of the connecting portion. The second shorter side is formed as a curved side curved at a center portion thereof toward the center side of the groove for hydrodynamic bearing formation region (curved so that the convex portion of the curved side projects toward the center side). Further, the side walls of the first longer side, second longer side, first shorter side and second shorter side of each groove for hydrodynamic bearing 71 are all formed as inclined faces inclined so as to expand toward the opening face (downwardly, in a direction toward the impeller). The gradient of each side face preferably is the same as that described above with respect to the grooves for hydrodynamic bearing 38.

The gradients of the side walls of the first longer side, second longer side, first shorter side and second shorter side of the grooves for hydrodynamic bearing 71 are substantially equal to each other. The gradients of the side walls of the first longer side, second longer side, first shorter side and second shorter side of the grooves for hydrodynamic bearing 71 may not be equal to each other, but may be different from each other as described above in connection with the groove for hydrodynamic bearing 38.

In the second grooves for hydrodynamic bearing 71, although the entire side wall of the grooves for hydrodynamic bearing 71 is preferably formed as an inclined side wall, the side wall is not limited to this configuration, but may be an inclined side wall which is inclined obliquely such that the groove for hydrodynamic bearing begins expanding toward the opening face of the groove for hydrodynamic bearing 71 beginning at a portion spaced a predetermined distance (a relatively small distance) toward the opening face from the bottom face of the groove for hydrodynamic bearing 71, similarly to that of the grooves for hydrodynamic bearing 38 shown in FIG. 18 and described above. Further, where a groove for hydrodynamic bearing of such a type as just described is used, the form of the groove for hydrodynamic bearing preferably has a configuration the same as that shown in FIG. 18 and described above including the relationship between the width W3 of the inclined side wall portion and the groove for hydrodynamic bearing depth (H3+H4) and so forth.

In the centrifugal blood pump device 1 of the present embodiment, the resultant force of the attracting force between the first magnetic member 25 and the magnet 33 (impeller rotation torque generation section 3) (in FIG. 3, downwardly acting force) and the attracting force between the second magnetic member 29 and the permanent magnet 41 (in FIG. 3, upwardly acting force) is preferably set such that it is zero at a substantially center position of the housing 20 which is a movable range of the impeller 21. That is, the attracting force between the first magnetic member 25 and the magnet 33 (downwardly acting force in FIG. 3) and the attracting force between the second magnetic member 29 and the permanent magnet 41 (upwardly acting force in FIG. 3) maintains the impeller 21 at a center position between the portions of the housing located above and below the impeller 21. By this configuration, within any movable range of the impeller 21, the acting force by the attracting force to the impeller 21 is very low. As a result, since the friction resistance upon relative slipping between the impeller 21 and the housing 20 which is generated upon starting of rotation of the impeller 21 can be made relatively low, the surfaces of the two members upon the relative slipping suffer from little damage (roughening of the surface). Even where the dynamic pressure upon low speed rotation is relatively low, the impeller 21 can rather easily float in a contactless state from the housing 20. There is the possibility that hemolysis or thrombus may be caused by relative slipping between the impeller 21 and the housing 20, and there is also the possibility that thrombus by a slight surface damage (roughening) generated upon the relative slipping may be generated. Therefore, a configuration or arrangement causing attracting forces to act on the impeller from the opposite sides as seen in FIG. 1 and balancing those attracting forces with each other to minimize the resultant force to reduce the contact pressure between the impeller 21 and the housing 20 effectively addresses these concerns.

Although the impeller auxiliary attracting section 4 is configured from the magnetic member 29 disposed on the impeller and the permanent magnet 41 disposed on the housing, the impeller auxiliary attracting section 4 is not limited to this arrangement. For example, a permanent magnet may be disposed on the impeller while a magnetic member which exhibits attracting force cooperating with the permanent magnet is disposed on the housing side.

To prevent reduction of the rigidity of the impeller arising from the attracting force between the magnetic member 29 and the permanent magnet 41 in the impeller auxiliary attracting section 4, the opposing faces of the magnetic member and the permanent magnet which oppose each other preferably have different sizes from each other. The permanent magnets 41 are smaller than the magnetic member 29, and the sizes of the opposing faces of the magnets 41, 29 are different from each other. Consequently, the variation amount of the attracting force which varies depending upon the distance between them, that is, the negative rigidity, is suppressed to a relatively low level to prevent reduction of the impeller supporting rigidity.

Figure 13:
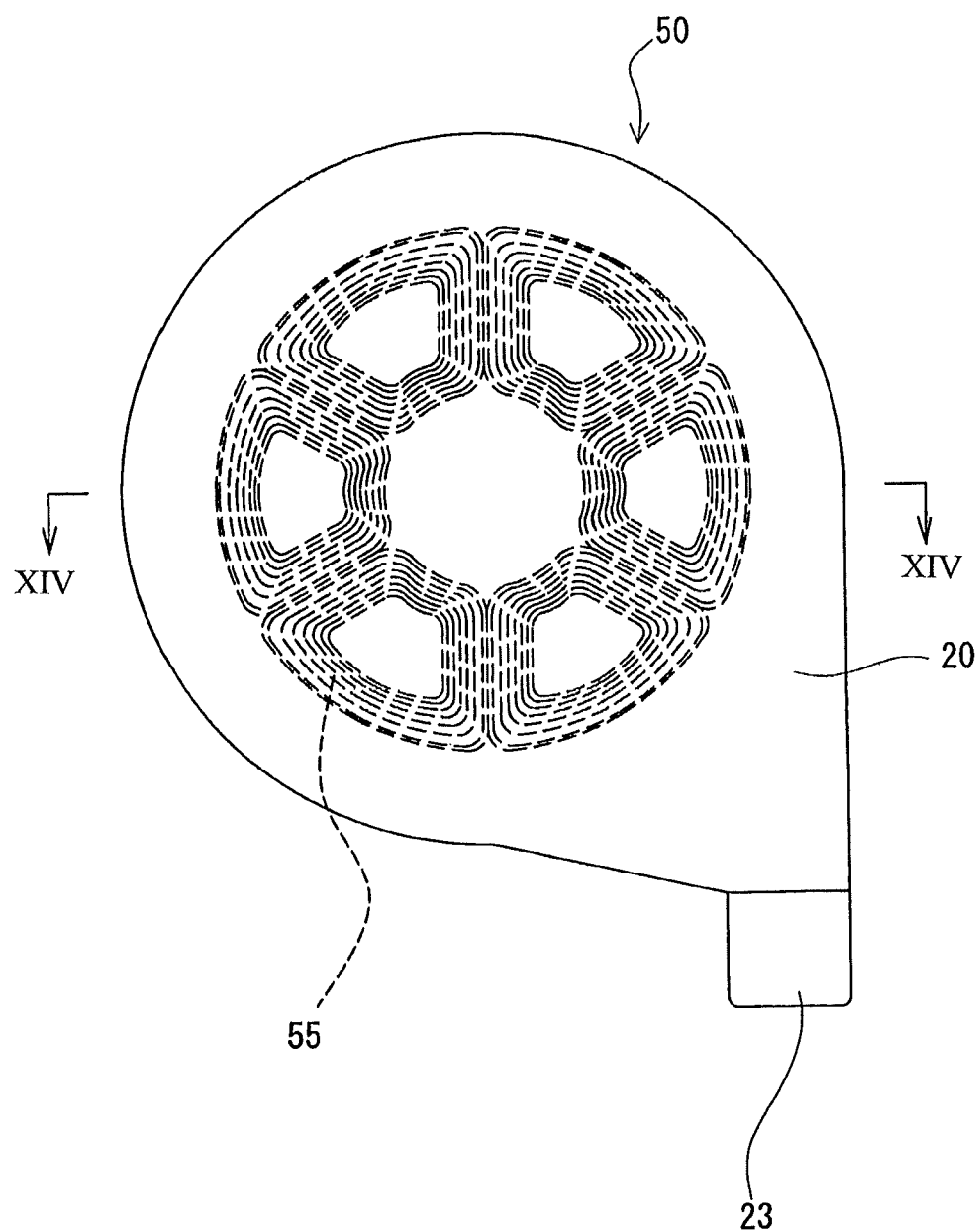
FIG. 13 is a bottom plan view of a further embodiment of a centrifugal blood pump device disclosed here.
Figure 14:
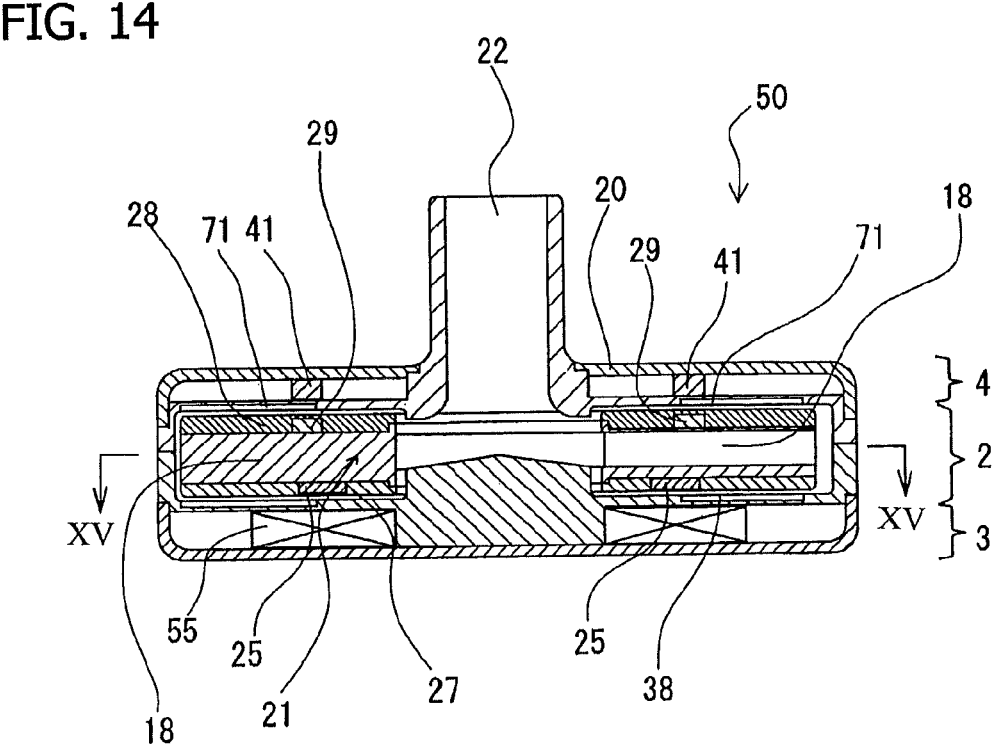
FIG. 14 is a cross-sectional view taken along the section line XIV-XIV in FIG. 13.
Figure 15:
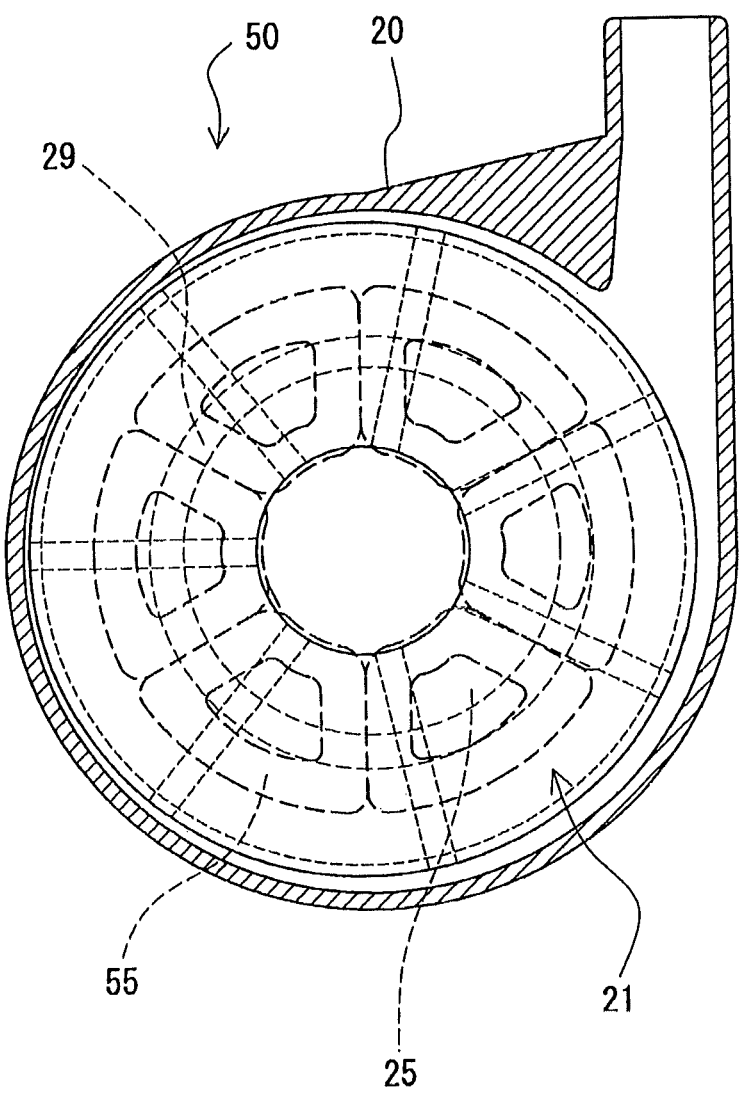
FIG. 15 is a cross-sectional view taken along the section line XV-XV in FIG. 14, with an impeller being represented by an outer appearance.

Set forth next with reference to FIGS. 13-15 is a description of a centrifugal blood pump device of a further embodiment disclosed here. The substantial difference between the centrifugal blood pump device 50 of the present embodiment and the centrifugal blood pump device 1 of the embodiment described above resides in the mechanism of the impeller rotation torque generation section 3. The impeller rotation torque generation section 3 in this second embodiment of the centrifugal blood pump device 50 of the present embodiment does not include a so-called rotor, but is of a type in which the impeller is driven directly. Also in the pump device 50 of the present embodiment, the impeller 21 rotates without contacting the housing inner face by pressure generated by the grooves for hydrodynamic bearing upon rotation. The following description focuses primarily upon the differences between this second embodiment and the embodiment described above. Features associated with the second embodiment of the centrifugal blood pump device 50 that are the same as features in the centrifugal blood pump device 1 described above are identified by common reference numerals and a detailed description of such features is not repeated. It is to be noted that the form of the grooves for hydrodynamic bearing 38 in this second embodiment of the centrifugal blood pump device 50 is same as that in the first embodiment described above.

The centrifugal blood pump device 50 of this second embodiment has the impeller rotation torque generation section 3 which includes a plurality of stator coils 55 accommodated in the housing 20 as shown in FIGS. 13 to 15. The plural stator coils 55 are circumferentially disposed such that they substantially exhibit (i.e., extend over) an equal angle with respect to the center axis of the circumference. In particular, six stator coils are provided. In this embodiment, multilayer stator coils are used as the stator coils. Changing the direction of the current flowing through each stator coil 55 generates a rotating magnetic field, and the impeller is attracted and rotated by the rotating magnetic field.

As shown in FIG. 14, a plurality of (for example, 6 to 12) magnetic members 25 (permanent magnets, follower magnets) are embedded in the impeller 21. In the present embodiment, the magnetic members 25 are embedded in a lower shroud 27. The embedded magnetic members 25 (permanent magnets) cooperate with the stator coils 55 of the impeller rotation torque generation section 3 to attract the impeller 21 to the opposite side to the blood inflow port 22 to couple with operation of the stator coils 55 and transmit rotation torque.

Embedding a certain number of magnetic members 25 as in the present embodiment sufficiently assures a magnetic coupling with the stator coils 55 as described below. The magnetic members 25 (permanent magnets) preferably have a substantially trapezoidal shape. The magnetic members 25 may have any of a ring shape and a plate shape. Further, the number and the arrangement form of the magnetic members 25 preferably correspond to the number and the arrangement form of the stator coils. The plural magnetic members 25 are disposed on a circumference such that the magnetic poles thereof may be different alternately and besides may be positioned at substantially equal angles with respect to the center axis of the impeller.

Figure 16:
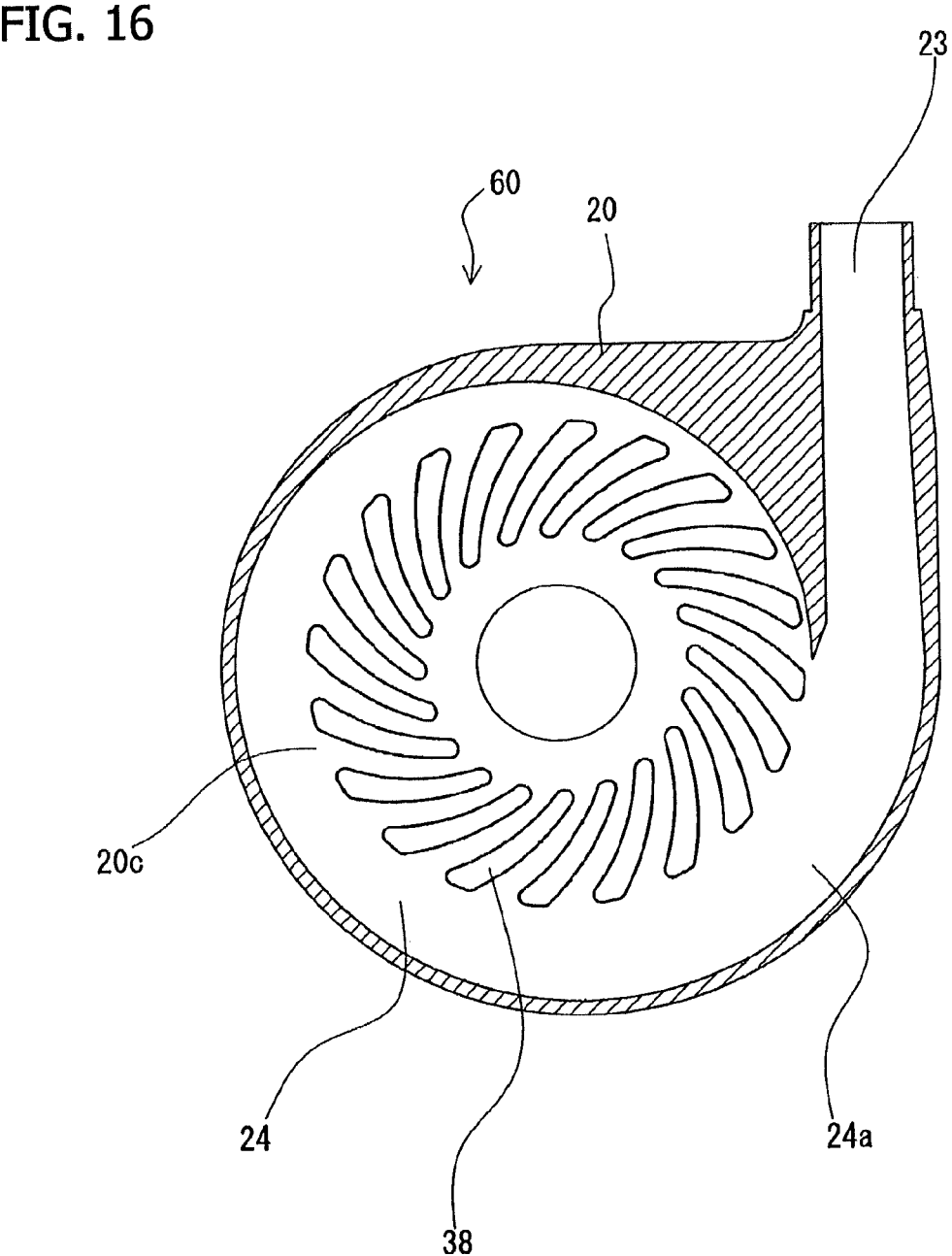
FIG. 16 is a transverse cross-sectional view of a still further embodiment of a centrifugal blood pump device disclosed by way of example here.

In the embodiment described above, substantially no volute is provided. But in all embodiments described above, the blood pump section may include a volute 24*a* which surrounds the impeller rotation region 20*c* and has a width increasing toward the blood outflow port 23 like a centrifugal blood pump device 60 of a still further embodiment shown in FIG. 16.

Figure 17:
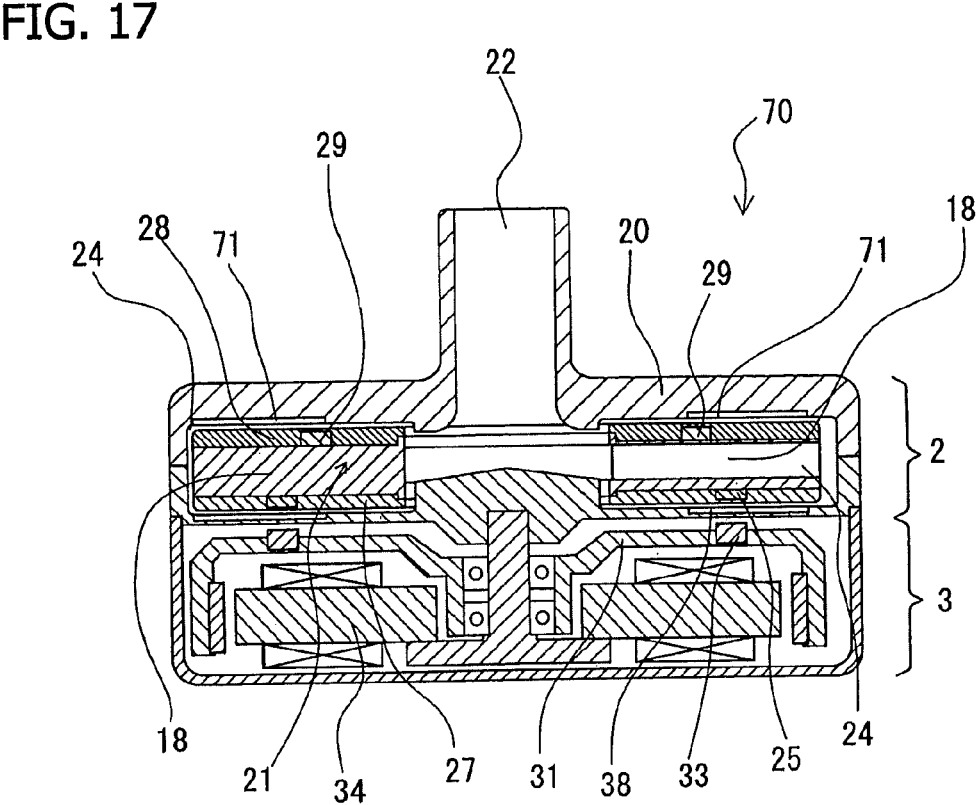
FIG. 17 is a longitudinal cross-sectional view of a yet further embodiment of a centrifugal blood pump device.

The embodiments of the centrifugal blood pump device described above include the impeller auxiliary attracting section 4. But in all embodiments described above, the impeller auxiliary attracting section can be eliminated to embody a configuration such as the centrifugal blood pump device 70 of a yet further embodiment shown in FIG. 17. The centrifugal blood pump device 70 is illustrated as including the second grooves for hydrodynamic bearing 71, but the centrifugal blood pump device 70 can be configured so that it does not include such second grooves for hydrodynamic bearing.

The centrifugal blood pump device disclosed here generally includes: a housing having a blood inflow port and a blood outflow port; a centrifugal pump section having a magnetic member and an impeller which rotates in the housing to send blood by centrifugal force upon rotation; an impeller rotation torque generation section for attracting and rotating the impeller of the centrifugal pump section; and a plurality of grooves for hydrodynamic bearing disposed on a housing inner face on the impeller rotation torque generation section side or on a face of the impeller on the impeller rotation torque generation section side, in which the impeller is rotated in a non-contacting state with respect to the housing by the grooves for hydrodynamic bearing, and each of the grooves for hydrodynamic bearing has an inclined side wall inclined obliquely such that the groove for hydrodynamic bearing is expanded toward an opening face of the groove for hydrodynamic bearing from a bottom face of the groove for hydrodynamic bearing or from a location displaced by a predetermined distance from the bottom face to the opening face side of the groove for hydrodynamic bearing.

The side wall of the groove for hydrodynamic bearing may be an inclined side wall inclined obliquely such that the groove for hydrodynamic bearing is expanded from the bottom face of the groove for hydrodynamic bearing toward the opening face of the groove for hydrodynamic bearing.

The groove for hydrodynamic bearing can be configured to include a first longer side and a second longer side extending from a peripheral edge toward the center side of the groove for hydrodynamic bearing formation region and opposing to each other, a first shorter side interconnecting end portions of the first longer side and the second longer side on the peripheral edge side of the groove for hydrodynamic bearing formation region, and a second shorter side interconnecting end portions of the first longer side and the second longer side on the center side of the groove for hydrodynamic bearing formation region.

The second shorter side is a curved side curved at a center portion thereof toward the center side of the groove for hydrodynamic bearing formation region.

The first longer side and the second longer side are arcuate longer sides curved in the same direction, the first longer side is positioned forwardly in the curved direction while the second longer side is positioned rearwardly in the curved direction, and a connecting portion between the second longer side and the first shorter side is formed in an arc having a center point on the inner side of the connecting portion and in the proximity of the connecting portion.

The centrifugal blood pump device can also be configured so that the side wall of the first longer side portion, the side wall of the second longer side portion, the side wall of the first shorter side portion and the side wall of the second shorter side portion is an inclined side wall forming an obtuse angle with respect to the bottom face of the groove for hydrodynamic bearing.

The impeller of the centrifugal blood pump device includes a second magnetic member, the centrifugal blood pump device includes a floating assisting mechanism for magnetically attracting the second magnetic member of the impeller to the opposite side to the impeller rotation torque generation section to assist floating of the impeller in the housing, and grooves for hydrodynamic bearing on the floating assisting mechanism side provided on the housing inner face on the opposite side to the impeller rotation torque generation section or on a face of the impeller on the opposite side to the impeller rotation torque generation section, and a side wall of each of the grooves for hydrodynamic bearing on the floating assisting mechanism side is an inclined side wall inclined obliquely such that the groove for hydrodynamic bearing is expanded from a bottom face of the groove for hydrodynamic bearing toward an opening face of the groove for hydrodynamic bearing.

The impeller rotation torque generation section can include a rotor having a magnet for attracting the magnetic member of the impeller and a motor for rotating the rotor, and the grooves for hydrodynamic bearing are provided on the housing inner face on the rotor side or on a face of the impeller on the rotor side. Or the impeller rotation torque generation section can include a plurality of stator coils disposed on a circumference for attracting the magnetic member of the impeller and rotating the impeller, and the grooves for hydrodynamic bearing are provided on the housing inner face on the stator coils side or on a face of the impeller on the stator coils side.

The detailed description above describes features and aspects of embodiments of a centrifugal blood pump device. But the invention here is not limited to the precise embodiments and variations described above and illustrated in the drawing figures. Changes, modifications and equivalents can be implemented without departing from the spirit and scope of the invention as defined in the accompanying claims. It is expressly intended that all such changes, modifications and equivalents which fall within the scope of the claims are embraced by the claims.

What is claimed is:

1. A centrifugal blood pump device comprising:
a housing possessing a blood inflow port opening to outside the housing and a blood outflow port opening to outside the housing;
a blood chamber inside the housing in fluid communication with the blood inflow port and the blood outflow port;
a rotatable impeller positioned in the blood chamber and rotatable in the blood chamber to send blood, which has entered the blood chamber from the blood inflow port, by centrifugal force to the blood outflow port:
a magnetic member fixed to the impeller so that the magnetic member rotates together with the impeller;
an impeller rotation torque generation section positioned on one axial end of the impeller to attract and rotate the impeller positioned in the blood chamber;
a plurality of grooves for forming a hydrodynamic bearing that are disposed either on an inner face of the housing which faces toward the impeller or on a face of the impeller which faces toward the impeller rotation torque generation section and configured to permit rotation of the impeller in a non-contacting state with respect to the housing; and
each of the grooves being defined by a first side wall and a second side wall opposite the first side wall, the first side wall extending from a groove opening face and a groove bottom face and inclined to form a first obtuse angle with respect to the groove bottom face, and the second side wall extending from the groove opening face and the groove bottom face and inclined to form a second obtuse angle with respect to the groove bottom face that is different than the first obtuse angle,
wherein the first sidewall has a first edge and a second edge,
wherein the second sidewall has a third edge and a fourth edge,
wherein a third sidewall extends between the first edge and the third edge,
wherein a fourth sidewall opposite the third sidewall extends between the second edge and the fourth edge,
wherein a portion of the third side wall extending from the groove opening face and the groove bottom face is inclined at the first obtuse angle with respect to the groove bottom face, and wherein a portion of the fourth side wall extending from the groove opening face and the groove bottom face is inclined at the second obtuse angle with respect to the groove bottom face.

2. The centrifugal blood pump device according to claim 1, wherein the housing is cylindrically shaped the blood inflow port projects perpendicularly from a center portion of an upper face of the housing, and the blood outflow port projects tangentially from a side face of the cylindrically shaped housing.

3. The centrifugal blood pump device according to claim 1, wherein the grooves are located in a hydrodynamic bearing formation region which possesses a center and a peripheral edge located radially outwardly of the center, each of the grooves including:
a first longer side and a second longer side both extending from adjacent the peripheral edge toward the center of the hydrodynamic bearing formation region,
the first and second longer sides being positioned in opposing relation to each other,
the first and second longer sides each possessing one end portion located closer to the peripheral edge than the center of the hydrodynamic bearing formation region,
the first and second longer sides also possessing another end portion located closer to the center than the peripheral edge of the hydrodynamic bearing formation region;
a first shorter side extending from the one end portion of the first longer side toward to the one end portion of the second longer side; and
a second shorter side extending from the other end portion of the first longer side toward to the other end portion of the second longer side.

4. The centrifugal blood pump device according to claim 3, wherein the second shorter side of each groove is a curved side possessing center portion that is curved so that a convexly shaped surface of the center portion faces toward the center of the hydrodynamic bearing formation region.

5. The centrifugal blood pump device according to claim 3, wherein the first longer side and the second longer side are arcuate longer sides curved in a common curved direction, the first longer side is positioned forwardly in the curved direction while the second longer side is positioned rearwardly in the curved direction, and further comprising an arc-shaped connecting portion between the second longer side and the first shorter side, the arc-shaped connecting portion possessing a center point on an inner side of the connecting portion and in proximity of the arc-shaped connecting portion.

6. The centrifugal blood pump device according to claim 1, wherein the magnetic member is a first magnetic member fixed to the impeller, and the grooves are first grooves, further comprising:
- a second magnetic member fixed to the impeller to rotate together with the impeller;
- a floating assisting mechanism for magnetically attracting the second magnetic member of the impeller in a direction opposite the impeller rotation torque generation section to assist floating of the impeller in the housing;
- the floating assisting mechanism including second grooves for forming a hydrodynamic bearing provided on an inner face of the housing on an opposite side to the impeller rotation torque generation section or on a face of the impeller on the opposite side to the impeller rotation torque generation section; and
- a side wall of each of the second grooves is an obliquely inclined side wall expanding outwardly from a bottom face of the second groove toward an opening face of the second groove.

7. The centrifugal blood pump device according to claim 1, wherein the impeller rotation torque generation section includes a rotor to which is fixed a magnet for attracting the magnetic member of the impeller, and a motor for rotating the rotor, and the grooves being provided either on an inner face of a portion of the housing that faces the impeller and that is positioned between the impeller and the rotor or on a face of the impeller which faces in a direction toward the rotor.

8. The centrifugal blood pump device according to claim 1, wherein the impeller rotation torque generation section includes a plurality of circumferentially arranged stator coils for attracting the magnetic member of the impeller and for rotating the impeller, and the grooves being provided either on an inner face of a portion of the housing that faces the impeller and that is positioned between the impeller and the stator coils or on a face of the impeller which faces in a direction toward the stator coils.

* * * * *